United States Patent [19]
Brown et al.

[11] Patent Number: 5,790,256
[45] Date of Patent: Aug. 4, 1998

[54] FOOT ANALYZER

[75] Inventors: Algie C. Brown, Atlanta; Carl T. Welty, Chamblee, both of Ga.; Henry G. Williams, III, Lexington, Va.; David M. Williams, Dunwoody; James M. Dabbs, Duluth, both of Ga.

[73] Assignee: Footmark, Inc., Atlantic, Ga.

[21] Appl. No.: 792,407

[22] Filed: Feb. 3, 1997

Related U.S. Application Data

[63] Continuation of Ser. No. 718,205, Sep. 20, 1996, abandoned, which is a continuation of Ser. No. 221,707, Apr. 1, 1994, abandoned, which is a continuation-in-part of Ser. No. 903,017, Jun. 23, 1992, Pat. No. 5,361,133.

[51] Int. Cl.$^6$ .................................................. G02B 26/08
[52] U.S. Cl. ........................ 356/376; 33/3 R; 33/6; 33/515; 73/172; 600/592; 364/558
[58] Field of Search ........................... 356/372, 376, 356/379, 383, 384; 33/3 A, 3 B, 3 C, 3 R, 6, 515; 12/146 L, 146 M; 73/172, 765; 364/550, 558, 561; 600/535, 592, 595

[56] References Cited

U.S. PATENT DOCUMENTS

| | | | |
|---|---|---|---|
| 2,043,187 | 6/1936 | Owens | 128/2 |
| 2,975,519 | 3/1961 | Berlin, Jr. et al. | 33/3 |
| 3,066,417 | 12/1962 | Samuels | 33/3 C |
| 3,325,799 | 6/1967 | Farris | 340/279 |
| 3,328,882 | 7/1967 | Blivice | 33/3 |
| 3,457,647 | 7/1969 | Cohen et al. | 33/3 |
| 3,727,606 | 4/1973 | Sielaff | 128/25 |
| 3,926,177 | 12/1975 | Hardway, Jr. et al. | 128/25 |
| 3,941,137 | 3/1976 | Vredenbregt et al. | 128/423 |

(List continued on next page.)

OTHER PUBLICATIONS

Foot Analyzer Specification 1, Brown et al., prior to Apr. 1, 1994.
Mini Emed System; Novel Eletronics, Inc. brochure, Feb. 1989.
BTE Dynamic Pedobarograph Foot Pressure Analysis Syst.; Baltimore Therapuetic Eq.Co.; 1990.
Advertisement for "Advance 2000 Bed" Hospitals American Hospital Piblushing, Inc., Hillenbrand Ind.; Mar. 1992.
Foot–Fitter; Toshiba; Operations Guide 1991.
Alexander et al.; The Assessment of Dynamic Foot-To-Ground Contact Forces & Plantar Pressure Dist. vol. 11 #3; Dec. 1990.

(List continued on next page.)

*Primary Examiner*—Hoa Q. Pham
*Attorney, Agent, or Firm*—Troutman Sanders LLP; R. Stevan Coursey, Esq.

[57] ABSTRACT

An apparatus and methods for analyzing feet which utilize matrixes of pressures sensors and optical sensors connected to a controller and a monitor. An apparatus of the invention includes a housing which houses a controller and a monitor and defines left and right foot wells for receiving left and right feet, respectively. The floor of each foot well includes a pressure pad assembly which includes a matrix of pressure sensor contacts covered by a variably resistive pressure pad to form pressure sensor matrixes. A digital signal processor normalizes and smoothes the pressure data for display on the monitor. Infrared LED's and phototransistors are located around the perimeter of each foot well and are utilized to measure the length, width, and heights of a foot. A microprocessor addresses each LED and phototransistor separately. The controller reads data created by the DSP and IR microprocessor, calculates additional data, and displays the resulting data on the monitor. According to one method, the pressure sensors and optical sensors are utilized to determine, among others, foot length, foot width, shoe size, foot volume, foot shape, force distribution, pronation, arch type, and recommended last type. In other methods, the DSP and IR microprocessors provide data which enable the controller to perform calculations and comparisons to display orthotic prescriptions or insole selection information, as well as medical information related to center of pressure and postural sway analysis which is useful in diagnosing and treating a large variety of medical problems.

9 Claims, 25 Drawing Sheets

U.S. PATENT DOCUMENTS

| | | | |
|---|---|---|---|
| 4,134,063 | 1/1979 | Nicol et al. | 324/61 R |
| 4,169,462 | 10/1979 | Strube | 128/721 |
| 4,267,728 | 5/1981 | Manley et al. | 73/172 |
| 4,294,014 | 10/1981 | Baumann et al. | 33/3 C |
| 4,381,788 | 5/1983 | Douglas | 128/722 |
| 4,395,826 | 8/1983 | Bidegain et al. | 33/3 C |
| 4,432,223 | 2/1984 | Paquette et al. | 73/7 |
| 4,437,138 | 3/1984 | Nicol | 361/283 |
| 4,449,264 | 5/1984 | Schwartz | 12/1 |
| 4,499,394 | 2/1985 | Koal | 310/330 |
| 4,510,636 | 4/1985 | Phillips | 12/1 |
| 4,517,457 | 5/1985 | Valasek et al. | 250/239 |
| 4,517,696 | 5/1985 | Schartz | 12/1 |
| 4,520,581 | 6/1985 | Irwin et al. | 36/88 |
| 4,530,124 | 7/1985 | Somner | 12/12.4 |
| 4,538,353 | 9/1985 | Gardner | 33/3 C |
| 4,598,717 | 7/1986 | Pedotti | 128/779 |
| 4,604,807 | 8/1986 | Bock et al. | 33/3 C |
| 4,644,801 | 2/1987 | Kustanovich | 73/172 |
| 4,703,217 | 10/1987 | Ratzlaff et al. | 310/338 |
| 4,703,445 | 10/1987 | Dassler | 364/561 |
| 4,736,312 | 4/1988 | Dassler et al. | 364/561 |
| 4,745,290 | 5/1988 | Frankel et al. | 250/560 |
| 4,745,930 | 5/1988 | Confer | 128/779 |
| 4,760,850 | 8/1988 | Phillips et al. | 128/432 |
| 4,763,287 | 8/1988 | Gerhaeuser et al. | 364/561 |
| 4,771,394 | 9/1988 | Cavanagh | 364/561 |
| 4,813,436 | 3/1989 | Au | 128/779 |
| 4,814,661 | 3/1989 | Ratzlaff et al. | 310/328 |
| 4,827,763 | 5/1989 | Bourland et al. | 73/172 |
| 4,858,621 | 8/1989 | Franks | 128/779 |
| 4,876,758 | 10/1989 | Rolloff et al. | 12/142 |
| 4,895,160 | 1/1990 | Reents | 128/671 |
| 4,956,628 | 9/1990 | Furlong | 340/323 |
| 4,996,012 | 2/1991 | Gierschewski et al. | 264/40.1 |
| 5,025,476 | 6/1991 | Gould et al. | 356/374 |
| 5,033,291 | 7/1991 | Padoloff et al. | 73/172 |
| 5,040,313 | 8/1991 | Simjian et al. | 36/114 |
| 5,049,079 | 9/1991 | Furtado et al. | 434/253 |
| 5,080,109 | 1/1992 | Arme, Jr. | 128/782 |
| 5,088,503 | 2/1992 | Seitz | 128/779 |
| 5,088,504 | 2/1992 | Benesh et al. | 128/781 |
| 5,107,854 | 4/1992 | Knotts et al. | 128/779 |
| 5,118,112 | 6/1992 | Bregman et al. | 273/183 |
| 5,128,880 | 7/1992 | White | 356/376 |
| 5,134,999 | 8/1992 | Osipov | 128/661.03 |
| 5,150,902 | 9/1992 | Heisler | 273/187.1 |
| 5,164,793 | 11/1992 | Wolfersberger et al. | 356/376 |
| 5,186,062 | 2/1993 | Roost | 73/865.4 |
| 5,195,030 | 3/1993 | White | 364/401 |
| 5,206,804 | 4/1993 | Thies et al. | 364/401 |
| 5,210,897 | 5/1993 | Reedmann et al. | 12/7 |
| 5,216,594 | 6/1993 | White et al. | 364/403 |
| 5,221,088 | 6/1993 | McTeigue et al. | 273/187.2 |
| 5,230,249 | 7/1993 | Sasaki et al. | 73/714 |
| 5,231,723 | 8/1993 | White et al. | 12/133 |
| 5,237,520 | 8/1993 | White | 364/560 |
| 5,361,133 | 11/1994 | Brown et al. | 356/376 |

OTHER PUBLICATIONS

Quantitive Evaluation of Sway As An Indicator of Functional Balance in Post–Traumatic Brain Injury, Lehmann et al., Arch Phys. Medical Rehab vol. 71–Nov. 1990.

AMTI'S AccuSway™Platform–A Force Platform Designed Specifically For Measurement of Postural Sway–Advanced Mechanical Technology, Inc.–Prior to Apr. 1, 1994.

Dynamic Features of Standing & Their Correlation With Neurological Disorders–Scand J. Rehab 59–64; 1978.

Balance Performance; Force Production & Activity Levels In Noninstrutionalized Men 60–90 yrs. of Age Iverson et al. Physical Therapy /vol. 70, Nov. 6/Jun. 1990–pp. 23–30.

The Effects of Simulated Knee–Flexion Contractures On Standing Balance; Porter et al–AMJ. Phys. Med. Rehab. vol. 69 No. 3 Jun. 1990–pp. 144–147.

Quantification of Postural Sway In Normals & Patients With Cerebellar Diseases–Diener et al.–Electroencephalography & Clinical Neurophysiology 1984 57: 134–142.

Normal Subject Postural Sway During the Romberg Test Black et al. Am. Jor. of Otolaryngology–1982 pp. 309–318.

Linear Models For The Prediction of Stature From Foot & Boot Dimensions–Gordon et al.–Jor. of Forensic Sc.–May 1992. Predictors & Prognosis of Inability To Get Up After Falls Among Elderly Persons–JAMA Jan. 6, 1993 vol. 269 #1 pp. 65–70.

Treatment of Parkinson Disease–Donald B. Calne–Drug Therapy –vol. 329 #14 pp.1021–1078 Sep. 30, 1993.

Emed Systems; Novel Electronics, Inc. brochure, Feb., 1989.

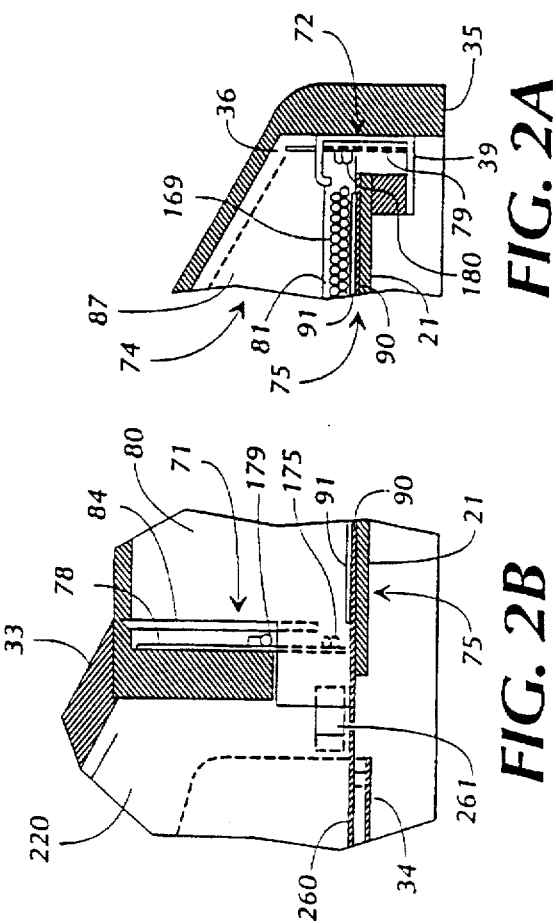
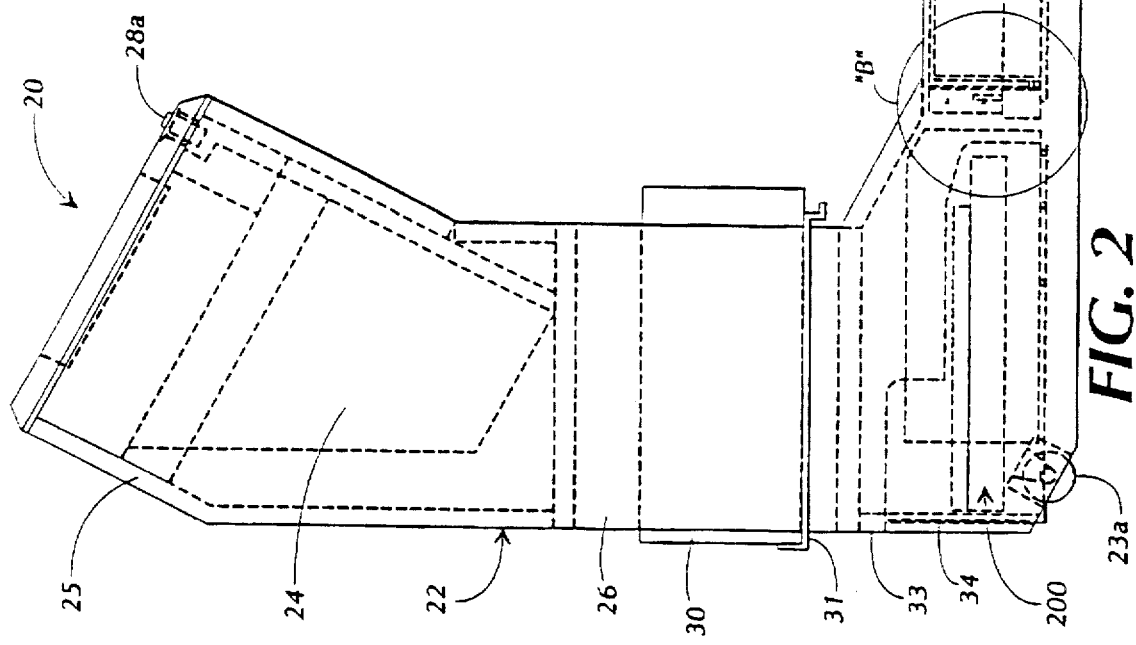

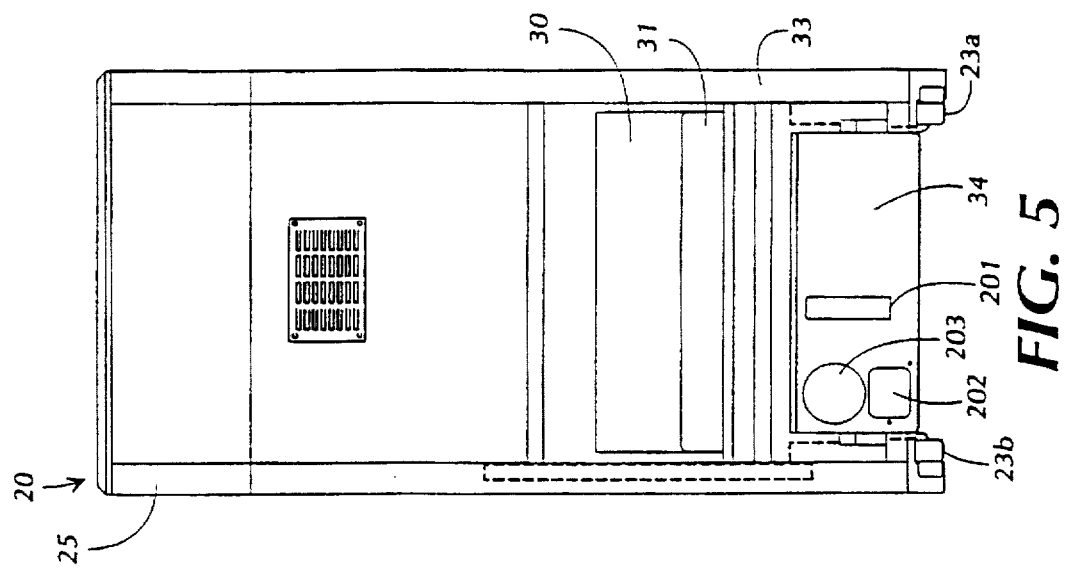
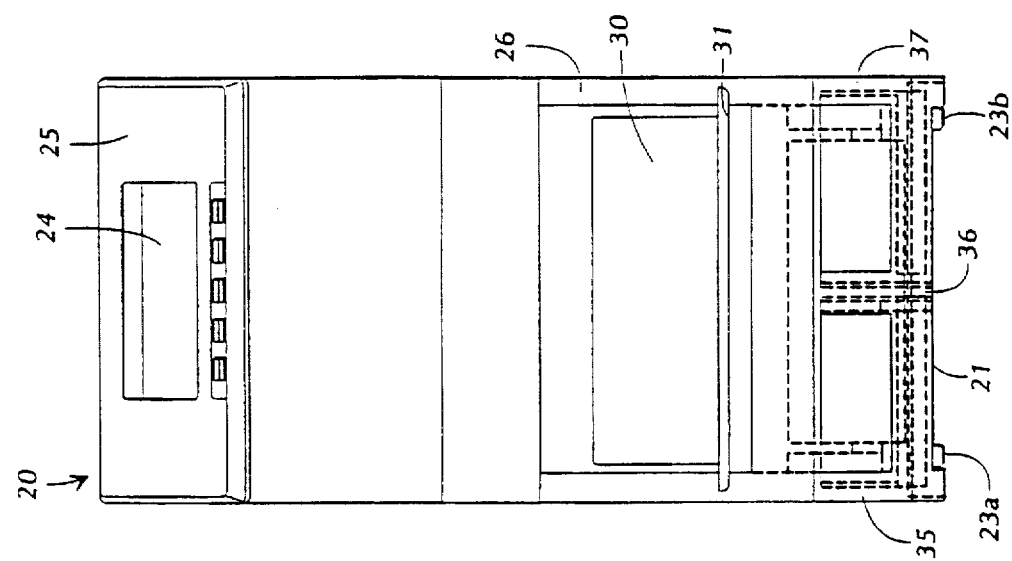
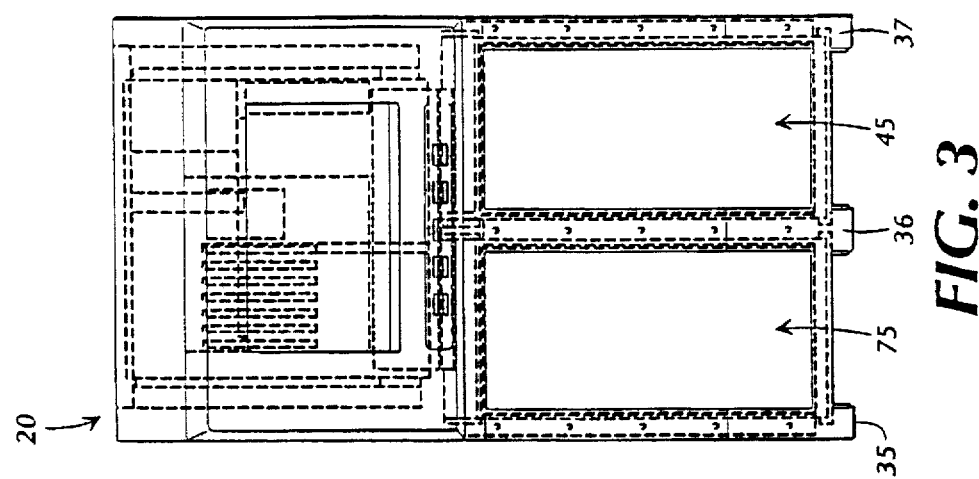

FOOT ANALYZER

CROSS-REFERENCE TO RELATED APPLICATION

This application is a continuation of application Ser. No. 08/718,205, filed on Sep. 20, 1996, which is a continuation of application Ser. No. 08/221,707, filed on Apr. 1, 1994, both abandoned, which is a continuation-in-part of application Ser. No. 07/903,017, filed on Jun. 23, 1992, U.S. Pat. No. 5,361,133.

BACKGROUND OF THE INVENTION

The present invention relates generally to the field of foot analysis, and more specifically, to the fields of automatically measuring foot dimensions, forces, and movements.

It is well known that shoes and feet come in a variety of sizes and shapes. Consequently, in order to provide a particular consumer with a pair of shoes, a shoe retailer must determine that particular consumer's shoe size. If the consumer is unaware of his or her shoe size, the shoe retailer typically measures the consumer's feet to determine the appropriate shoe size. One of the most commonly used devices for measuring feet for fitting shoes is the Branach device. This manual device includes two levers slidably mounted upon a labeled platform for determining the length and width of a particular foot. Since shoes have traditionally been available in men, women, and children sizes, three different types of Branach devices, corresponding to each of these sizing schemes, have been utilized by shoe retailers. The manual nature of the Branach device, as well as the need for using three different devices for men, women, and children, suggest the need for a system which automatically measures all types of feet for fitting shoes.

Various types of automatic feet measuring devices have been developed in the past. Many of these devices are very expensive and time consuming and often utilize complex mechanical moving components which are subject to ordinary shortcomings of moving mechanical parts. Other devices include one or more light sources located to shine light onto the top or bottom of a foot to cast planar outlines of the foot onto light sensitive sensors which are monitored to produce foot length and width measurements. Although length and width measurements are useful and relatively easily obtained from such systems, additional desirable measurements which are difficult or impossible to obtain from such prior systems include, among others, foot height, foot volume, foot shape, and force distribution throughout the foot in a normal stance.

In addition to analyzing feet for fitting shoes, it has also been well known to analyze feet for various medical reasons. Force plates of various designs have previously been used to monitor changes of center of pressure and postural sway for various medical purposes, such as evaluating the effects of age, various neurological disorders (e.g. Parkinson's disease, Epilepsy), drug/alcohol/chemical abuse and use, and various injuries, such as limb, back or traumatic brain injuries, as well as evaluating the need and effect of various surgeries (such as determining how weight is being shifted before and after knee or hip surgery) and vocational rehabilitation. The center of pressure and postural sway objective information is known to be very useful in diagnosing and treating a large variety of medical problems. In addition, static analysis of center of pressure and postural sway has also been linked to predicting falls and a patient's ability to walk without injury. Unfortunately, many of the prior devices are expensive, difficult to use, and often provide little readily useful information. Another medical reason for analyzing feet relates to the processes of prescribing or selecting an orthotic, such as an insole. Such processes are often very subjective, expensive, time-consuming and inaccurate. While it is understood that a primary purpose of a foot sole/insole combination is to distribute forces applied to the foot, such a result is rarely reached without great effort.

There is a need, therefore, in the industry for a method and an apparatus for analyzing feet for these and other related, and unrelated, purposes.

SUMMARY OF THE INVENTION

Briefly described, the present invention, includes a preferred apparatus and a variety of preferred methods for analyzing feet. In one preferred embodiment, a method is provided for measuring feet for fitting shoes. An apparatus for accomplishing the inventive method includes a housing which houses a controller and a monitor and defines left and right foot wells for receiving left and right feet, respectively. The floor of each foot well includes a pressure pad assembly which includes a matrix of pressure sensor contacts covered by a variably resistive pressure pad to form a matrix of pressure sensors. Each pressure sensor is independently addressable and includes two contacts separated by an insulated gap which is selectively bridged by the pressure pad to effect an independently measurable, pressure-related resistance across the insulated gap.

A digital signal processor (DSP) is electrically positioned between the controller and the pressure sensors and controls operation of the pressure sensors. During operation, a reference voltage is driven onto one row at a time addressed through an analog multiplexer array. The resulting current flowing from one column addressed through a second analog multiplexer array is converted into an amplified analog voltage. Subsequently, the analog voltage is converted into a resulting digital representation. The DSP then references a table to convert the digital representation into pounds and thereafter transfers the raw pound data, one row at a time, to the controller through a first-in-first-out (FIFO) memory resource. The DSP also conditions each row of pound data for display on the monitor. A smoothing method and an auto-normalization method are also employed to provide more accurate and visually appealing monitor output screens.

Located around the inner perimeter of each foot well are optical sensors, consisting of infrared (IR) light emitting diodes (LED's) and corresponding phototransistors, which are utilized to measure the length, width, and heights of a foot. A microprocessor is electrically positioned between the controller and the optical sensors and controls operation of the optical sensors by addressing and driving the sensors through programmable array logic circuits (PAL's) and multiplexer arrays. According to the preferred method, one LED in each foot well is supplied a modulated current while a corresponding phototransistor is checked for receipt of the modulated signals.

Before a foot is placed in a foot well, the optical sensors operate in a scan mode which only checks every fifth LED/phototransistor pair. When a foot is placed in a foot well, thus blocking one of the optical sensors, the optical sensors enter into a tracking mode where the outer limits of the width, length, and height are tracked, thus saving time over repeatedly checking every optical sensor.

According to one preferred method of the present invention, when the foot wells are empty, the controller displays on the monitor a slide show of user defined screens.

When the optical sensors detect a foot and enter into the tracking mode, the controller reads data created by the DSP and IR microprocessor, calculates additional data, and displays the resulting data on the monitor. The pressure sensors and optical sensors are utilized to determine in a normal stance, among others, foot length, foot width, shoe size, foot volume, foot shape, force distribution, pronation, arch type, and recommended last type. The IR measurements begin with the leg and ankle and continue around the foot. Such determinations, along with intended use information obtained from the customer, are compared to a database of available shoes to determine recommended best fits for each customer. Such data can also be stored or transferred to an external system for storage with reference to each particular customer.

According to another preferred method of the present invention, the programming of the apparatus of the preferred embodiment is altered to calculate and display center of pressure information for postural sway analysis. In addition to displaying an initial pressure distribution screen similar to that of the first preferred method, the apparatus of this second preferred embodiment uniquely displays a center of pressure screen showing a center of pressure grid for each foot relative to an outline of that foot along with a combined center of pressure grid between the foot outlines. In addition, weight distribution per foot is shown along with graphs of radial displacement as measures of time and frequency. Each of the grids and graphs are capable of showing traces through time, as well as overlaying previous tests for particular patients. Also, depending on particular testing needs, instructional information and test result information may also be displayed.

According to yet another preferred method of the present invention, pressure and IR information are analyzed to prescribe a custom orthotic, or select a stock insole. Precise objective criteria, such as overall weight, pressure distribution, foot length, foot width, foot height, and foot volume are measured and compared with stored information related to shoe size and volume, cushioning and force absorption properties of various orthotic materials. A screen is displayed which diagrams the exact size and shape of the recommended orthotics or insoles for each foot. Furthermore, for composite orthotics, the thickness of each layer and the shape and location of each section of different material is shown along with a description of the material and its properties.

It is therefore an object of the present invention to provide a useful and precise apparatus for analyzing feet which includes pressure sensors and optical sensors.

Another object of the present invention is to provide a very fast and economical method and apparatus for analyzing feet.

Another object of the present invention is to provide a method and apparatus for analyzing feet which stores data useful in designing shoes which are more comfortable and protective of feet, particularly in designing lasts which are more accurately sized based upon precise measurements.

Another object of the present invention is to provide an apparatus for fitting shoes which includes a left pressure pad assembly and a right pressure pad assembly, wherein each pressure pad assembly includes a matrix of independent pressure sensors which share a variably resistive pressure pad.

Another object of the present invention is to provide a method for displaying a visual representation of a pressure matrix which includes auto-normalization and smoothing.

Yet another object of the present invention is to provide an apparatus for fitting shoes which includes, for each foot, length, width, and height matrixes of optical emitters located on one side and end of a foot well and corresponding length, width, and height matrixes of optical receivers located on an opposing side and end of the foot well.

Still another object of the present invention is to provide a method of using optical sensors to efficiently track outer profile boundaries of a foot.

Still another object of the present invention is to provide a method of integrating foot pressure data and optical profile data to fit shoes.

Still another object of the present invention is to provide a method of comparing foot measurements to a database of shoes to recommend suitable shoes.

Still another object of the present invention is to provide an apparatus and a method for analyzing feet which is useful in diagnosing and treating one or more of the above-described medical problems.

Still another object of the present invention is to provide an apparatus and a method for analyzing feet which displays center of pressure information for postural sway analysis.

Still another object of the present invention is to provide an apparatus and a method for analyzing feet which traces center of pressure and overlays previous patient results.

Still another object of the present invention is to provide an apparatus and a method for analyzing feet which displays a center of pressure grid within an outline of each foot in addition to a combined center of pressure grid.

Still another object of the present invention is to provide an apparatus and a method for analyzing feet which displays graphs against time and frequency of center of pressure radial displacement.

Still another object of the present invention is to provide an apparatus and a method for analyzing feet which prescribes an accomodative or protective custom orthotic based upon pressure and IR data.

Still another object of the present invention is to provide an apparatus and a method for analyzing feet which selects a stock insole based upon pressure and IR data.

Still another object of the present invention is to provide an apparatus and a method for analyzing feet which selects an orthotic or insole material based upon measured and calculated data and planned activity.

Still another object of the present invention is to provide an apparatus and a method for analyzing feet which recommends a shoe size and a shoe style based upon the shape and volume of a prescribed custom orthotic or a selected stock insole.

Still another object of the present invention is to provide an apparatus and a method for analyzing feet which shows the shape and dimensions of an orthotic for a patient.

These and other objects, features and advantages of the present invention will become apparent upon reading and understanding this specification, taken in conjunction with the accompanying drawings.

BRIEF DESCRIPTION OF THE DRAWINGS

FIG. 2 is a left side view of the apparatus of FIG. 1.

FIG. 3 is a top view of the apparatus of FIG. 1.

FIG. 4 is a front view of the apparatus of FIG. 1.

FIG. 5 is a rear view of the apparatus of FIG. 1.

DETAILED DESCRIPTION OF THE PREFERRED EMBODIMENT

Figure 1:
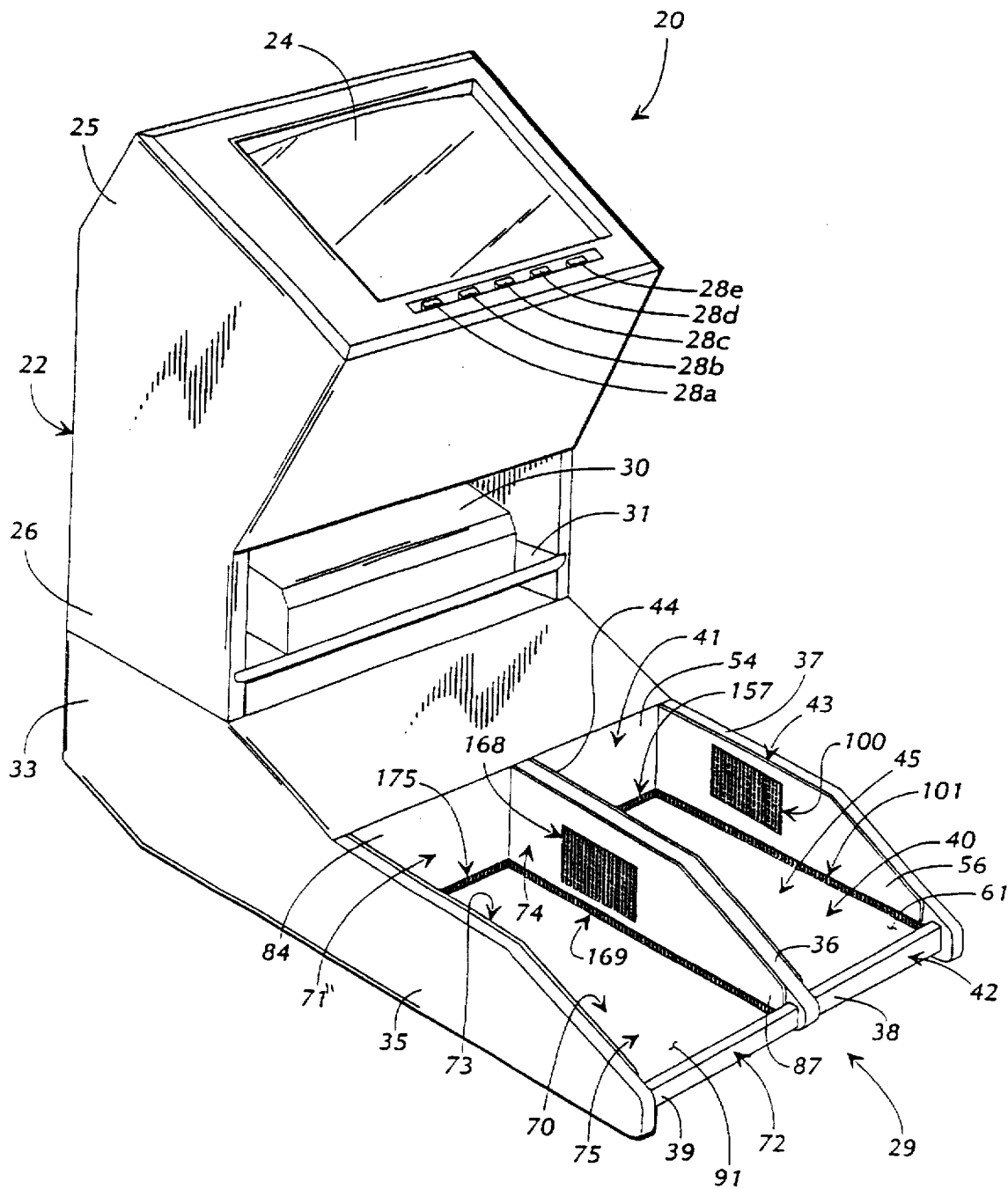
FIG. 1 is a perspective view of a foot analyzer in accordance with the preferred embodiments of the present invention.

Referring now to the drawings, in which like numerals represent like components throughout the several views, a foot analysis system 20, in accordance with the first preferred embodiment of the present invention, is shown in FIG. 1. A frame structure 22 is shown including a monitor housing 25 which houses a monitor 24 and supports lighted control buttons 28a–e. The frame structure 22 also includes a controller housing 33 and a printer housing 26 which houses a printer 30 resting on a slidably mounted printer shelf 31. Furthermore, the frame structure 22 includes a left panel 35 and a right panel 37 extending outward from the controller housing 33 to border a sensor assembly 29.

A left foot well 70 and a right foot well 40 are shown defined by the sensor assembly 70 between the left and right panels 35, 37. The floor of the left foot well 70 is represented as a left pressure pad assembly 75 including a left pad cover 91, and the floor of the right foot well 40 is represented as a right pressure pad assembly 45 including a right pad cover 61. Four infrared (IR) assemblies circumscribe each foot well 40, 70. Namely, a left front IR assembly 71, a left rear IR assembly 72, a left outer IR assembly 73, and a left inner IR assembly 74 circumscribe the left foot well 70, a right front right front IR assembly 41, a right rear IR assembly 42, a right outer IR assembly 43, and a right inner IR assembly 44 circumscribe the right foot well 40.

The left inner IR assembly 74 includes a left height transmitter array 168 and a left length transmitter array 169 mounted upon a left inner IR board 81 (substantially hidden from view), and the right outer IR assembly 43 includes a right height transmitter array 100 and a right length transmitter array 101 mounted upon a right outer IR board 50 (substantially hidden from view). Although hidden from view in FIG. 1, the left outer IR assembly 73 includes a correspondingly positioned left height receiver array 171 and a left length receiver array 172 mounted upon a left outer IR board 80, and the right inner IR assembly 44 includes a correspondingly placed right height receiver array 135 and a right length receiver array 136 mounted upon a right inner IR board 51. The left front IR assembly includes a left width receiver array 175 mounted upon a left front IR board 78 (substantially hidden from view), and the right front IR assembly 41 includes a right width receiver array 157 mounted upon a right front IR board 48 (substantially hidden from view). Likewise, although hidden from view in FIG. 1, the left rear IR assembly 72 includes a correspondingly placed left width transmitter array 180 mounted upon a left rear IR board 79, and the right rear IR assembly 42 includes a correspondingly placed right width transmitter array 125 mounted upon a right rear IR board 49.

A center panel 36 is shown extending between the left inner IR assembly 74 and the right inner IR assembly 44. The left inner IR assembly 74 further includes a left inner cover 87 which substantially obscures the underlying left inner IR board 81 and ends immediately above the left length transmitter array 169. The left inner cover 87 is generally opaque except for a clear portion positioned over the left height transmitter array 168. A right outer cover 56 included in the right outer IR assembly 43 is very similar to the left inner cover 87, and corresponding covers are included in the left outer IR assembly 73 and the right inner IR assembly 44. The left front IR assembly 71 and the right front IR assembly 41 include a left front cover 84 and a right front cover 54, respectively, which are completely opaque and extend downward to locations immediately above the left width receiver array 175 and the right front receiver array 157. The left rear IR assembly 72 and the right rear IR assembly 42 are shown including a left kick guard 39 and a right kick guard 38, respectively.

FIG. 2 shows a left side view of the foot analysis system 20. The monitor 24 is shown extending downward into the monitor housing 25 of the frame structure 22, and the printer 30 is shown resting on the printer shelf 31 mounted inside the printer housing 26. A controller 200 is shown mounted inside a controller drawer 34 which is slidably mounted inside the controller housing 33. One frame wheel 23a of two 23a,b is shown mounted to the underside of the controller housing 33 of the frame structure 22.

Figure 10A:
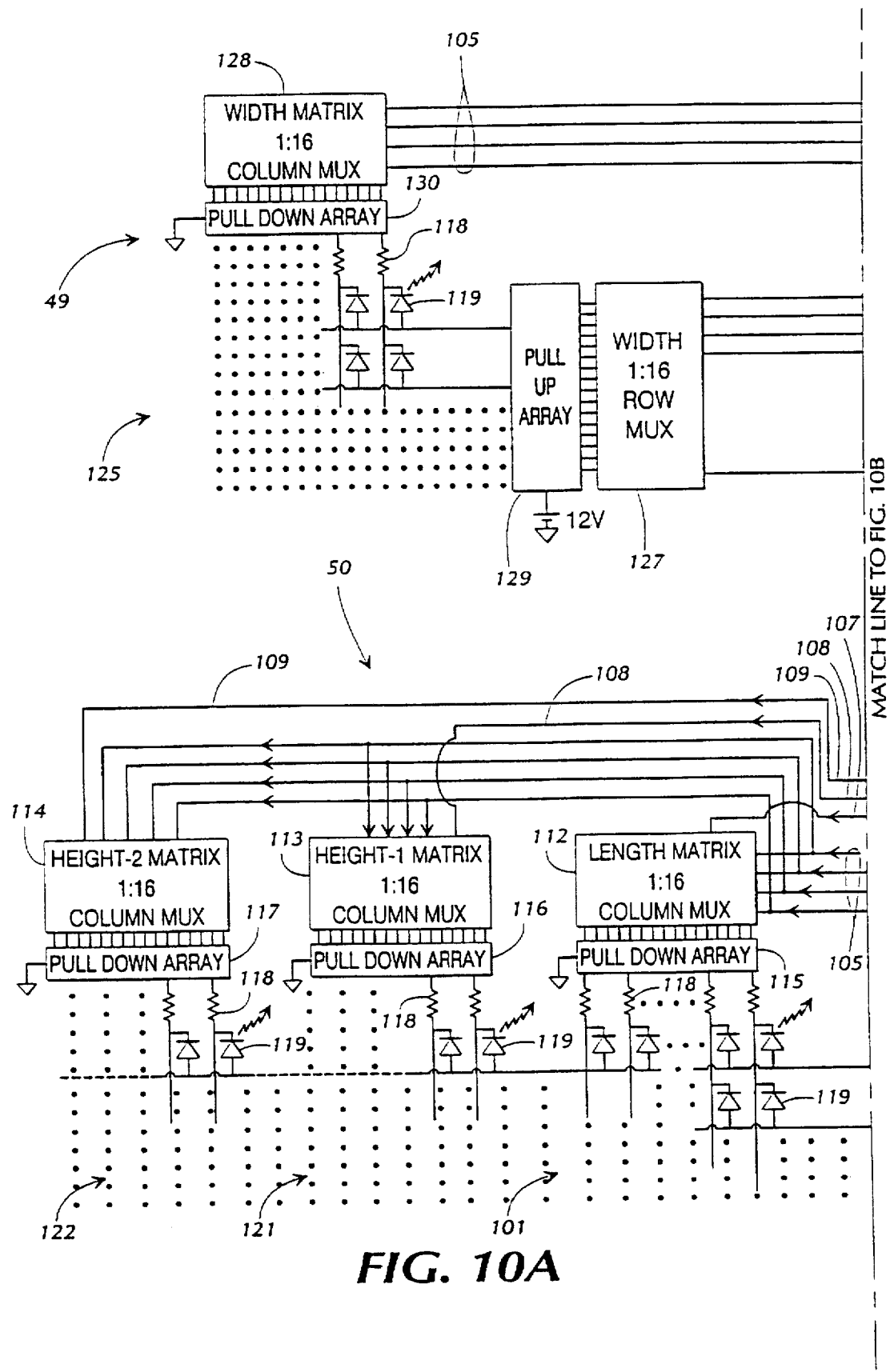
FIG. 10 is a block diagram representation of the right outer IR board and the right rear IR board of FIG. 6.
Figure 10B:
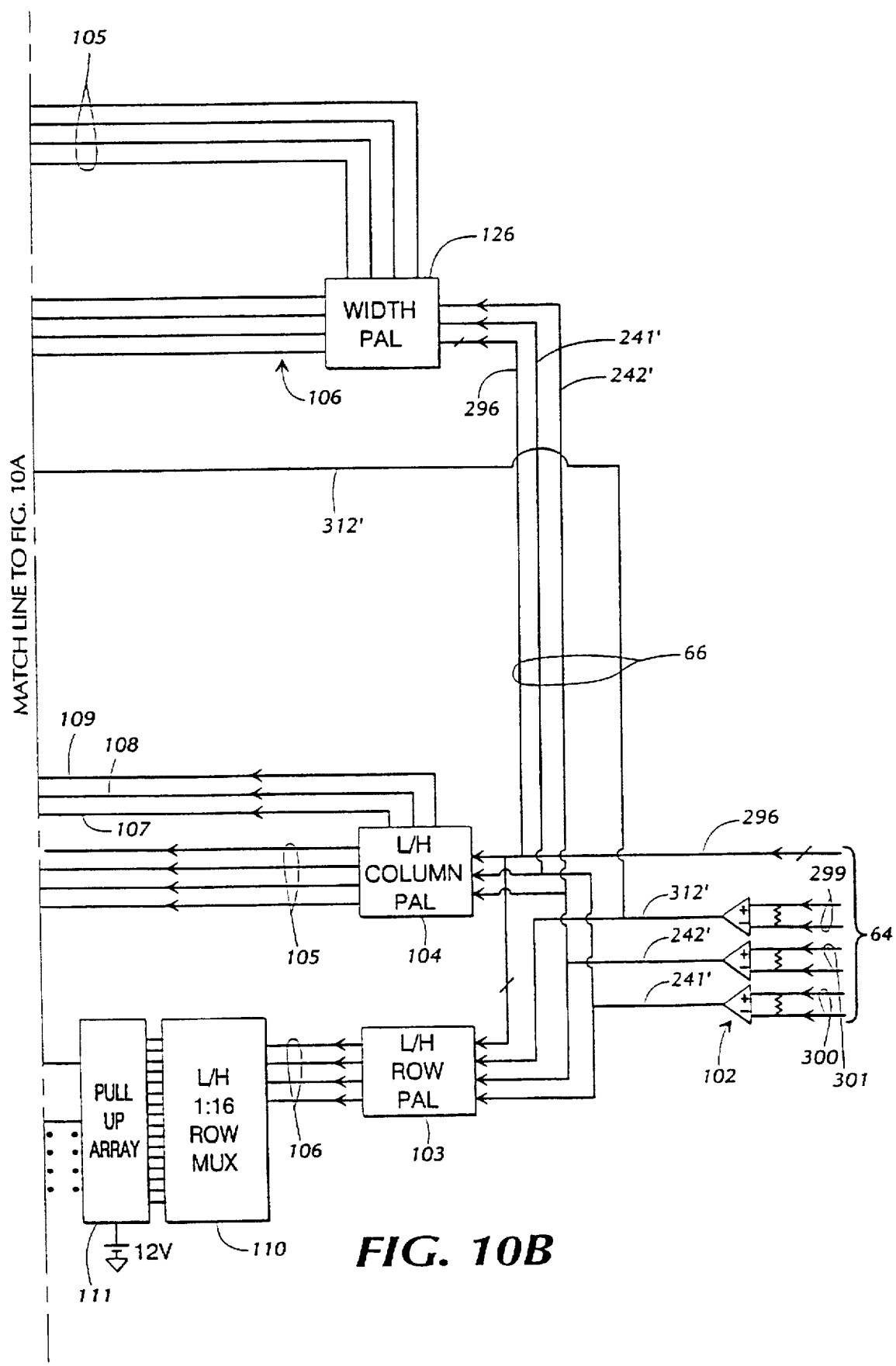

A more detailed view of the area designated as area "A" shows a cross-sectional view of the left panel 35, the left rear IR assembly 72, and the left pressure pad assembly 75. The left rear IR assembly 72 is shown including the left kick guard 39 and the left rear IR board 79, complete with the left width transmitter array 180. The left pressure pad assembly 75 is shown including a left pad contact board 90 and a left pad cover 91 which rest upon a mounting plate 21 which extends below the entire sensor assembly 29 and is supported by the kick guards 39, 38 (FIG. 1) and the left and right panels 35, 37 (FIG. 10). The left inner IR assembly 74 is also shown including the left inner cover 87 and the left inner IR board 81 interposed between the left inner cover 87 and the center panel 36 and upon which the left length transmitter array 169 is mounted.

A more detailed view of the area designated as area "B" shows a section immediately inside the left panel 35, behind the left outer IR board 80, and adjacent the controller housing 33. The mounting plate 21 is shown supporting the left pad contact board 90 and the left pad cover 91, and the left front IR assembly 71 is shown including a left gain boosting lamp 179 and the left width receiver array 175 mounted upon the left front IR board 78 which is behind the left front cover 84. A left sensor connector 261 is shown connecting the left pad contact board 90 to a mux board 260 which, as is discussed in greater detail below, is connected to a processor adapter 220 which connected to the controller 200 mounted inside the controller drawer 34.

FIGS. 3–5 show top, front, and rear views, respectively, of the foot analysis system 20. Both frame wheels 23a,b are shown in FIGS. 4 and 5. Also, a floppy drive 201, power supply 202, and fan 203 are shown extending through the controller drawer 34.

Figure 6:
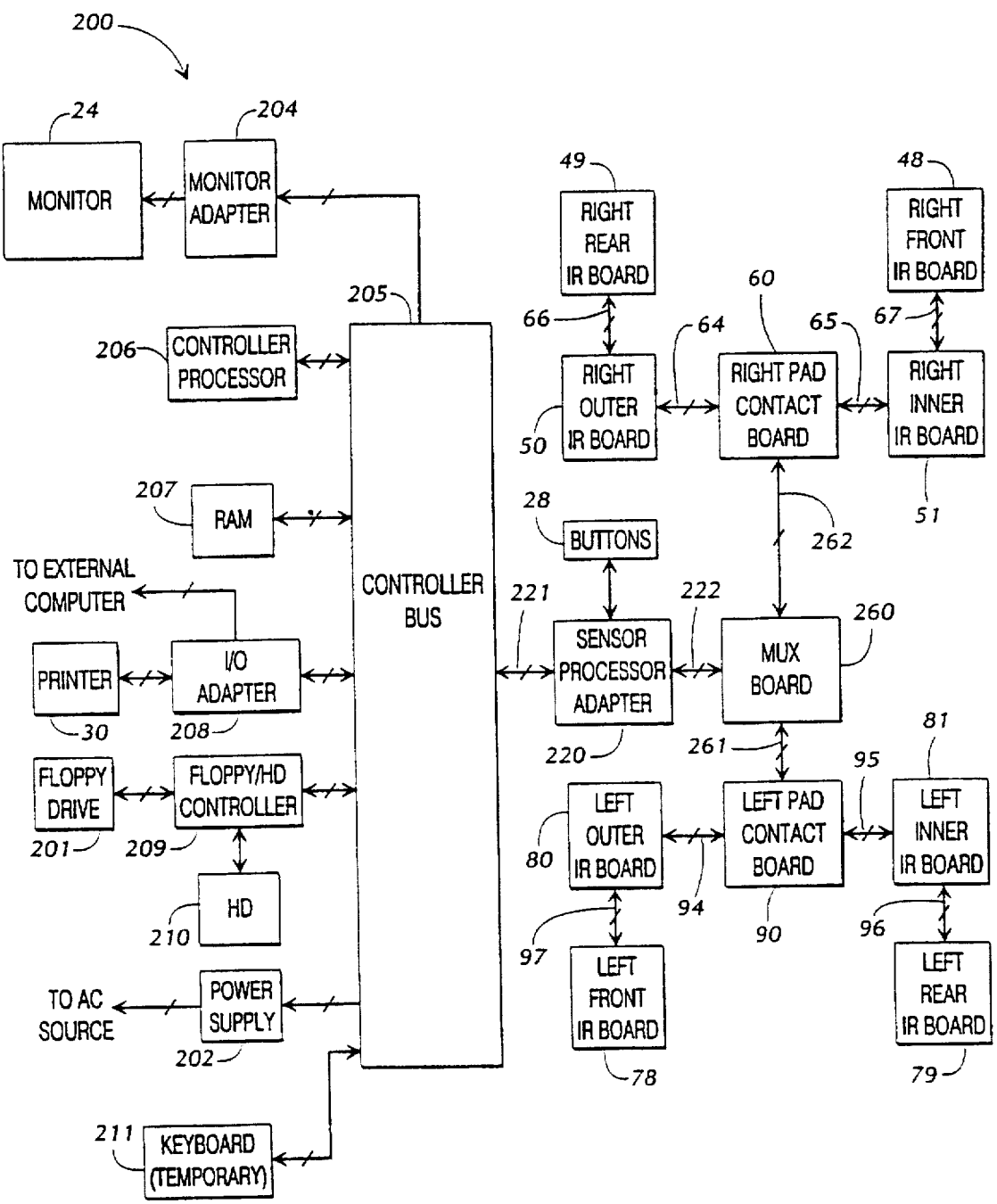
FIG. 6 is a block diagram representation of the electronic components of the apparatus for analyzing feet in accordance with the preferred embodiment of the present invention.

FIG. 6 shows a block diagram representation of the electronic components of the foot analysis system 20 in accordance with the first preferred embodiment of the present invention. The controller 200 is shown connected to the monitor 24 through a monitor adapter 204 which is connected to a controller bus 205. A controller processor 206 and random access memory (RAM) are also show connected to the controller bus 205. The printer 30 is shown connected to the controller bus 205 through an input/output (I/O) adapter 208 which also provides a link to any external computers or devices. The floppy drive 201 is shown connected to the controller bus 205 through a floppy/hard drive controller 209 which is also connected to a hard drive 210. The power supply 202 connects the controller 200 to an AC source, and a user may temporarily attach a keyboard for maintenance, testing, etc. One example of an acceptable controller 200 is an industry standard personal computer (PC) with an industry standard IBM® PC AT® bus.

The controller bus 205 is also connected through a sensor process-controller connector 221 to the sensor processor adapter 220, which is discussed in greater detail below. The buttons 28 are shown connected to the sensor processor adapter 220. The mux board 260, also discussed in greater below, is connected to the sensor processor adapter through a sensor processor-mux connector 222.

A right pad contact board 60 is connected to the mux board 260 through a right sensor connector 262, to the right outer IR board 50 through a right outer connector 64, and to the right inner IR board 51 through a right inner connector 65. The right rear IR board 49 is connected through a right rear connector 66 to the right outer IR board 50, and the right front IR board 48 is connected through a right front connector 67 to the right inner IR board 51. The left pad contact board 90 is connected to the mux board 260 through the left sensor connector 261, to the left outer IR board 80 through a left outer connector 94, and to the left inner IR board 58 through a left inner connector 95. The left rear IR board 79 is connected through a left rear connector 96 to the left inner IR board 81, and the left front IR board 78 is connected through a left front connector 97 to the left outer IR board 80. Each of the right boards 48–51, 60 are discussed in greater detail below. According to the first preferred embodiment of the present invention, the left boards 78–81, 90 are essentially identical to the corresponding right boards 48–51, 60, being interchangeable therewith, and are not discussed further.

Figure 7A:
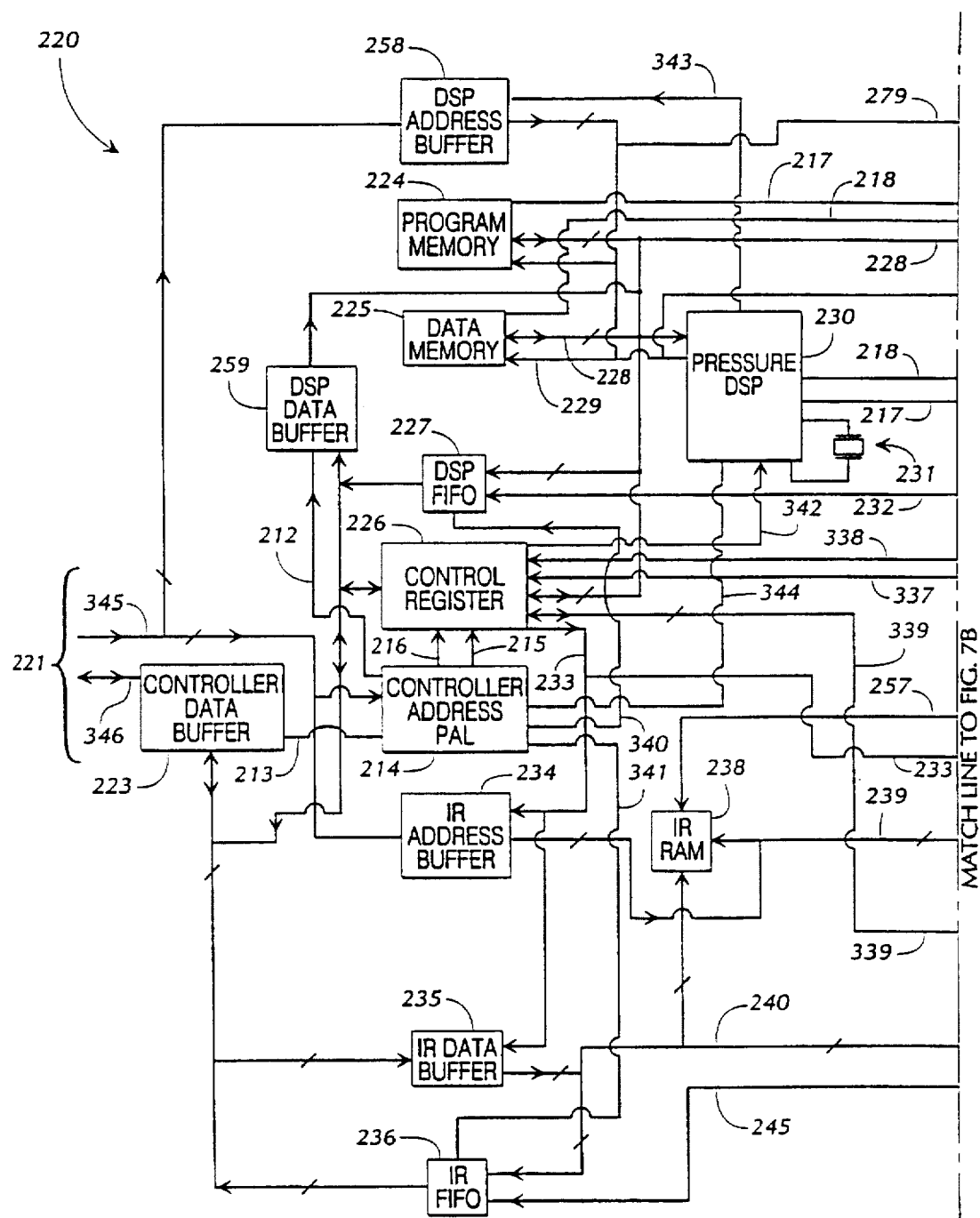
FIG. 7 is a block diagram representation of the sensor processor adapter and buttons of FIG. 6.
Figure 7B:
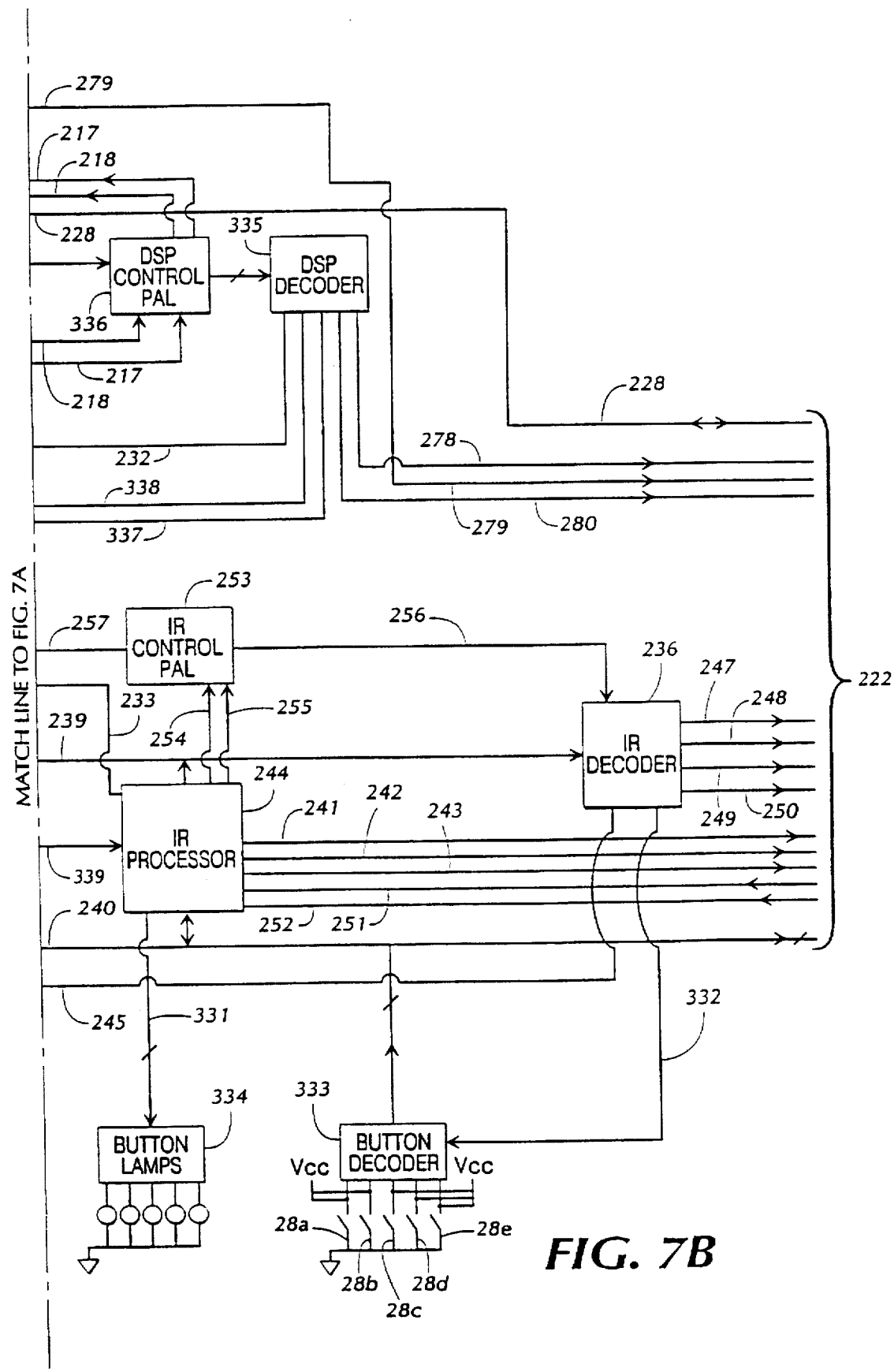

Refer now to FIG. 7, which shows a block diagram representation of the sensor processor adapter 220. The two central components of the sensor process adapter 220 are a digital signal processor (DSP) for the pressure system, denoted pressure DSP 230, and a microprocessor for the optical system, denoted IR processor 244. An example of an acceptable pressure DSP 230 is the ADSP-2105KP-40 from Analog Devices of Norwood, Mass. An example of an acceptable IR processor 244 is the MC68HC11F1FN from Motorola of Phoenix, Ariz. In alternate embodiments, the pressure DSP 230 and IR processor 244 are combined into a single processor.

The sensor processor-controller connector 221 is shown including, at least, a controller address bus 345 and a controller data bus 346. The controller address bus 345 is shown connected to a controller address programmable array logic (PAL) 214, an infrared (IR) address buffer 234, and a pressure address buffer 258. The controller data bus 346 is shown connected to a controller data buffer 223, through which the data bus 346 is connected to an IR first-in-first-out (FIFO) memory 236, an IR data buffer 235, a control register 226, a DSP FIFO 227, and a DSP data buffer 259.

The DSP address buffer 258 is connected to a DSP address bus 229 and gates the controller address buffer 345 onto the DSP address bus 229 upon receiving a control signal from the pressure DSP 230 along a bus grant line 343. One or more bits of the DSP address bus 229 are also connected to a program memory 224, a data memory 225, a DSP control PAL 336, and the sensor processor-mux connector 222 as read/convert selector 279. The DSP control PAL 336 is connected to the data memory 225 and program memory 224 through data memory select line 218 and program memory select 217, respectively, which originate with the pressure DSP 230. One or more bits of the DSP data bus 228 connect between the DSP data buffer 259, the program memory 224, the data memory 225, the DSP FIFO 227, the control register 226, the pressure DSP 230, and the sensor processor-mux connector 222. A DSP clock 231 is shown connected to the pressure DSP 230. The DSP decoder 335 is shown connected to the DSP FIFO through a FIFO written line 232, and to the control register 226 through read handshaking bit line 337 and write handshaking bit 338. The DSP controller 335 also connects to a row/column enable 278 and to an A-to-D enable 280 which exit the sensor processor adapter 220 through the sensor processor-mux connector 222.

The control register 226 represents a plurality of latches and buffers designed to interact with the controller address PAL 226 and other elements to control operation of the sensor processor adapter 220. The controller address PAL 214 is also connected to the DSP data buffer through DSP data buffer enable 212, to controller data buffer 223 through controller data buffer enable 213, to DSP FIFO 227 through DSP FIFO read enable 340, to the pressure DSP 230 through a DSP reset 344, and to the IR FIFO 236 through an IR FIFO read enable 341. The control register 226 sends signals along a DSP bus request 342 to the pressure DSP 230. The control register 226 is also connected through IR handshaking controls 339 to IR processor 244, and through IR address buffer select/IR process reset 233 to IR address buffer 234, IR data buffer 235, and IR processor 244.

One or more bits of an IR address bus 239 run between the IR address buffer 234, an IR RAM 238, the IR processor 244, and an IR decoder 236. Also, one or more bits of an IR data bus 240 run between the IR FIFO 236, the IR data buffer 235, the IR RAM 238, the IR processor 244, the button decoder 333, and the sensor processor-mux connector 222. A chip select program line 254 and a chip select general purpose line 255 connect the IR processor 244 to an IR control PAL 253 which, by virtue of the RAM chip select line 257, maps all writes from the IR data bus 240 into the IR RAM 238 and enables the IR decoder 236 for certain addresses on the IR address bus 239. Based on the address on IR address bus 240, the IR decoder 236 generates signals on the right receiver control 247, right transmit control 248, left receiver control 249, left transmit control 250 (all exiting the sensor processor adapter 220 through the sensor processor-mux connector 222), button decode enable 332 connected to the button decoder 333, or a write FIFO line 245 connected to the IR FIFO 236.

The IR processor 244 also generates signals to the button lamp control 334 through button lamp control lines 331. Also, the IR process 244 generates a serial peripheral interface (SPI) data signal 241, a right SPI clock 242, and a left SPI clock 243 which exit the sensor processor adapter 220 through the sensor processor-mux connector 222. Two signals, a right IR_seen 251 and a left IR_seen 252 are shown entering the IR processor from the sensor processor-mux connector 222.

Figure 8A:
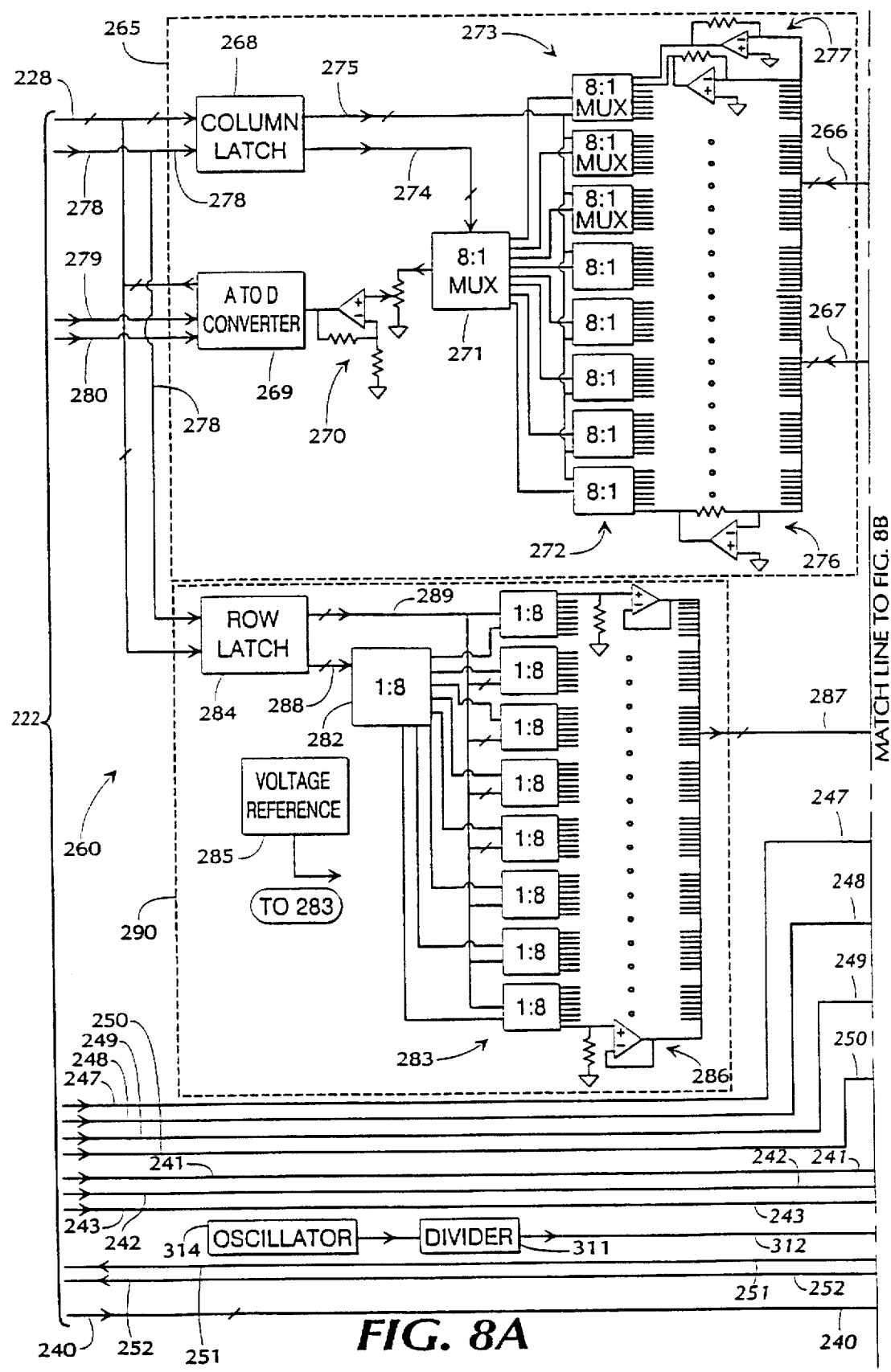
FIG. 8 is a block diagram representation of the mux board of FIG. 6.
Figure 8B:
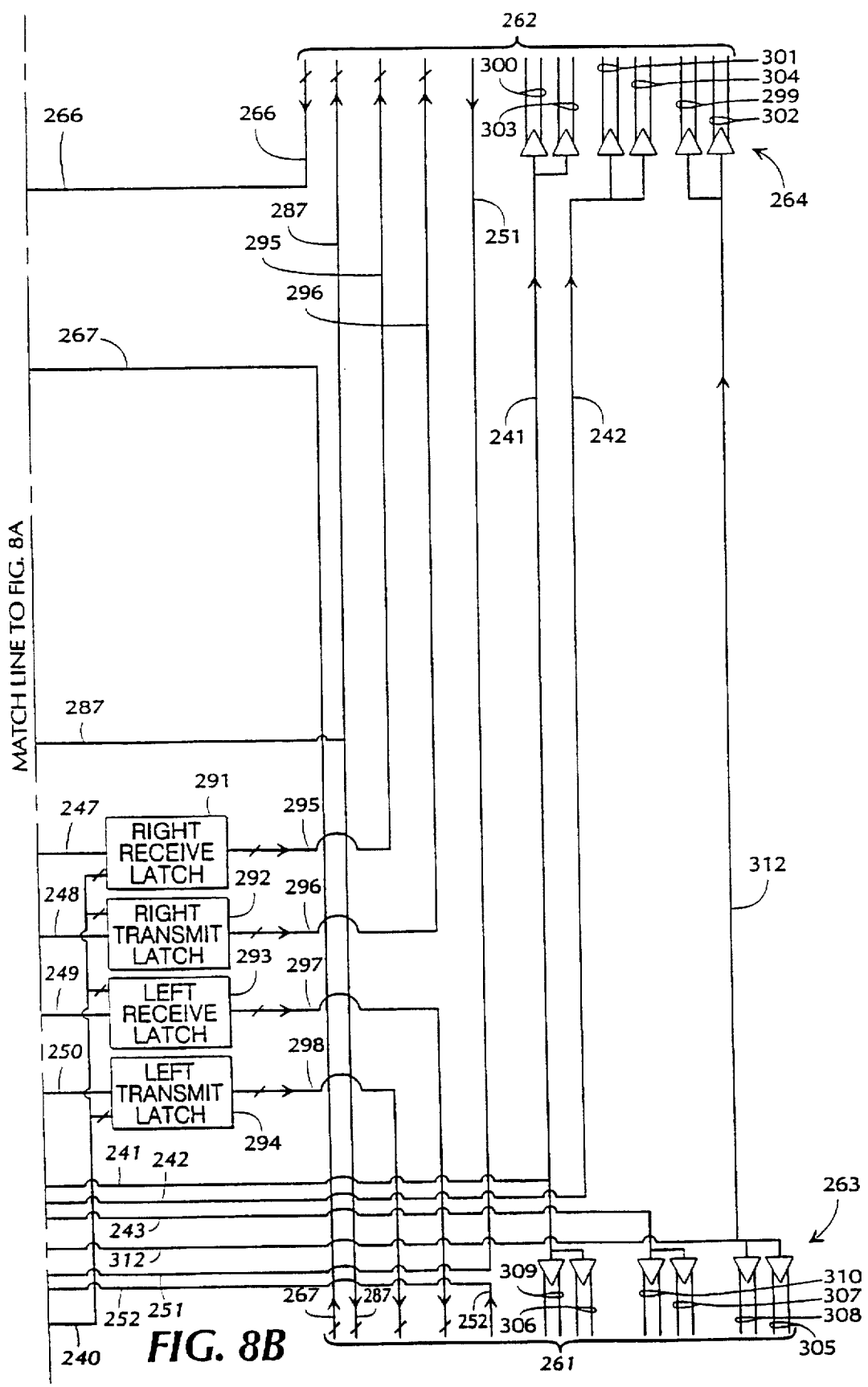

Refer now to FIG. 8, which shows a block diagram of the mux board 260 in accordance with the first preferred embodiment of the present invention. The sensor processor-mux connector 222 is shown including the identical lines leaving the sensor processor adapter 220. The DSP data bus 228, row/column enable 278, read/convert selector 279, and A-to-D enable 280 are shown connected to a column driver 265, and the DSP data bus 228 and row/column enable 278 are shown connected to a row driver 290. The column driver 265 includes a column latch 268 which receives input from the DSP data bus 228 and the row/column enable 278. An upper column mux select 274 connects the column latch 268 to an 8:1 analog multiplexer 271, and a lower column mux select 275 connects the column latch 268 to a lower column 8:1 analog mux bank 272, each of which are also connected to the 8:1 analog multiplexer 271. A left current to voltage (I-to-V) converter bank 276 of, in the preferred embodiments, 32 converters, supplies input from left column select lines 267 which exit the mux board 260 through the left sensor connector 261, and a right I-to-V convert bank 277 of, in the preferred embodiments, 32 converters, supplies input from right column select lines 266 which exit the mux board 260 through the right sensor connector 261. Output from the 8:1 analog mux 271 flows through a gain adjuster 270 and into the A-to-D converter 269 which supplies output onto the DSP data bus 228 according to control signals received through the read/convert selector and A-to-D enable 280.

The row driver 290 includes a row latch 284 receiving input from the DSP data bus 228 and the row column selector 278. An upper row mux select 288 connects the row latch 284 to an upper 1:8 mux 282, and a lower row mux select 289 connects the row latch 284 to a lower 1:8 analog mux bank 283, which also receive input from the upper 1:8 mux 282 and a voltage reference source 285 which, in the preferred embodiments, supplies −1.0 volts. The output from the lower 1:8 analog mux bank 283 is connected to a voltage source bank 286 of, in the preferred embodiments, 64 sources which are connected to row select lines 287 which exit the mux board through both the left and right sensor connectors 261, 262.

The right receive control 247, right transmit control 248, left receive control 249, and left transmit control 250 are shown connected to a right receive latch 291, a right transmit latch 292, a left receive latch 293, and a left transmit latch 294, respectively. One of these control lines 247–250 will cause one of these latches 291–294 to latch data from the IR data bus 240, which is also connected to each of the latches 291–294. Output from the latches 291–294 exit the mux board 260 along right receive matrix select 295, right transmit matrix select 296, left receive matrix select 297, and left transmit matrix select 298, respectively. An oscillator 314 is shown connected to a divider 311 with output along modulator line 312. The SPI data line 241, right SPI clock line 242, and left SPI clock line 243, along with the modulator line 312, are shown connected to a left differential driver bank 263 and/or a right differential driver bank 264 to convert the TTL signals into differential signals right transmit SPI data lines 300, right receive SPI data lines 303, right transmit SPI clock lines 301, right receive SPI clock lines 304, right transmit modulator lines 299, right receive modulator lines 302, left transmit SPI data lines 309, left receive SPI data lines 306, left transmit SPI clock lines 310, left receive SPI clock lines 307, left transmit modulator lines 308, and left receive modulator lines 305. The right and left IR_seen lines 251 and 252 are also shown passing through from the sensor connectors 262, 261 to the sensor processor-mux connector 222.

Figure 9A:
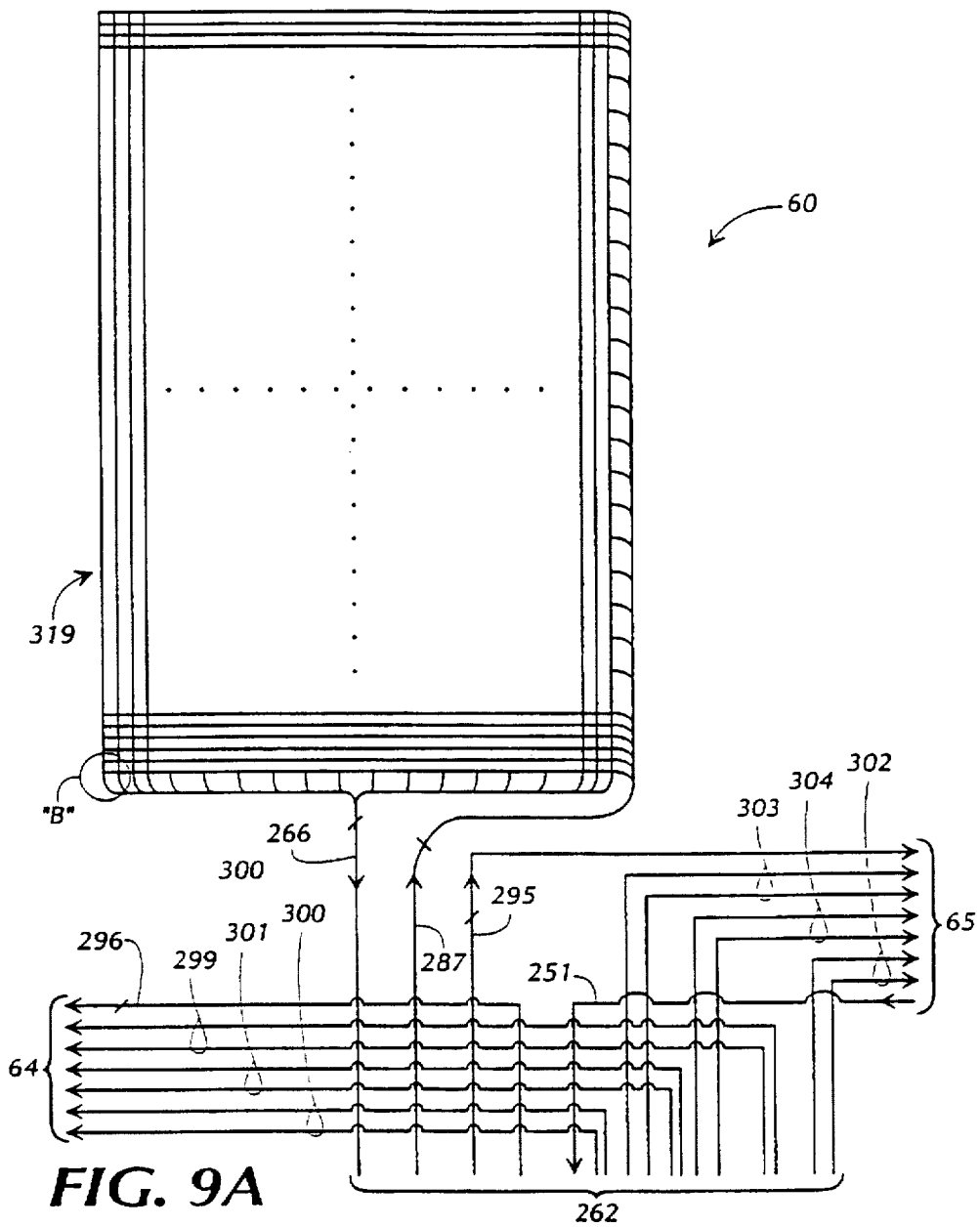
FIG. 9 is a block diagram representation of the right pad contact board of FIG. 6.
Figure 9B:
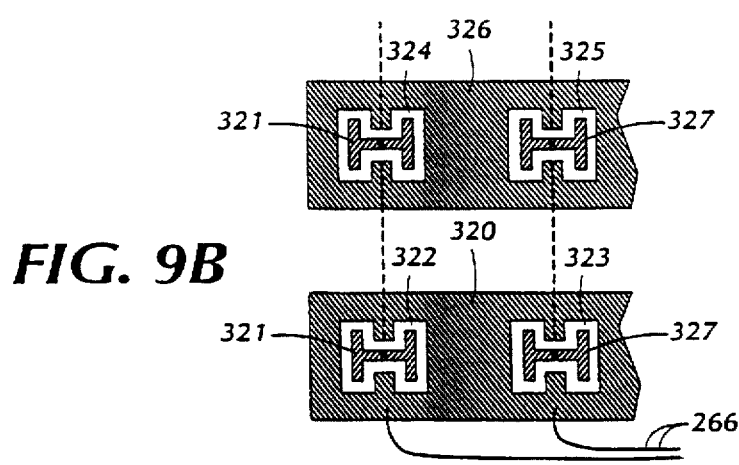

FIG. 9 shows a block diagram representation of the right pad contact board 60. The IR signals are shown passing through from the right sensor connector 262 to either the right outer connector 64 or right inner connector 65. The row select lines 287 are shown supplying current to the rows of a right contact array 319, and the right column select lines 266 are shown receiving current from the columns of the right contact array 319. The area designated as area "C" is shown in more detail to include a row 1 connector 320 and a row 2 connector 326 which define insulator gaps referred to as R1C1 insulator gap 322, R1C2 insulator gap 323, R2C1 insulator gap 324, and R2C2 insulator gap 325. Column 1 conductor 321 and column 2 conductor 327 are shown connected to the right column select lines 266 and protruding into the insulator gaps without touching the row conductors 320, 326. The right pad cover 61 (FIG. 1) bridges the insulator gaps to act as a matrix of pressure sensitive, variable resistors.

Refer now to FIG. 10, which shows a block diagram representation of the right outer IR board 50 and the right rear IR board 49. The right outer connector 64 includes the right transmitter matrix select 296, right transmit modulator lines 299, right transmit SPI clock lines 301, and right transmit SPI data lines 300. Each of the differential lines are converted back into TTL format through a TTL driver bank 102 to reproduce modulator line 312', right SPI clock line 242', and SPI data line 241'. Each of the reproduced lines, along with the right transmit matrix select 296 also proceed through the right rear connector 66 to the right rear IR board 49.

The right transmit matrix select 296 is connected along with the right SPI clock line 242' and SPI data line 241' to a length/height (L/H) column PAL 104, an L/H row PAL 103, and a width PAL 126. The modulator line 312' is connected to the L/H row PAL 103 and a width 1:16 row mux which is connected to the width PAL 126. The L/H column PAL 104 shifts the serial data coming from the SPI data line 241' into parallel format and sends the upper nibble through SPI upper nibble lines 105 to a length matrix column mux 112, a height-1 matrix column mux 113, and a height-2 matrix column mux 114 and enables each through length matrix select 107, height-1 matrix select 108, and height-2 matrix select 109 based upon data received through the right transmit matrix select 296. Similarly, the width PAL shifts the upper nibble of the SPI data to a width matrix column mux 128. The column mux's 112–114, 128 are shown connected to pulldown arrays 115–117, 130, which effectively pull selected columns down to ground through column resistors 118 upon selection. Examples of acceptable pull down arrays are ULN-2803 from Sprague of Worcester, Mass.

The L/H row PAL 103 also shifts the SPI data, but sends the lower nibble through lower nibble lines 106 to a L/H row mux 110 which is connected to a pull up array 111 which effectively supplies +12 volts to selected rows. Similarly, the width PAL 126 sends the SPI lower nibble to a width row mux 127 which is connected to a pull up array 129 which supplies +12 volts to selected rows. An example of an acceptable pull up array is the ULN 2981A, also from Sprague. The modulator line 312' modulates the row voltages to, in the preferred embodiments, 40 MHz to reduce errors due to outside light sources.

The columns from the pull down arrays 115–117, 130 and the rows from the pull up arrays 111 and 129 connect to transmitter light emitting diodes (LED's) 119 to form right length transmitter array 101, right height-1 transmitter array 121, right height-2 transmitter array 122, and right width transmitter array 125. Although electrically arranged in partially-to-completely filled 16×16 formats for efficient control, the arrays are physically arranged as described above with respect to FIG. 1. For example, the right height-1 and height-2 transmitter arrays 121, 122 combine physically to form the right height transmitter array 100 shown in FIG. 1. As current flows through the transmitter LED's 119, modulated, infrared light is emitted.

Figure 11A:
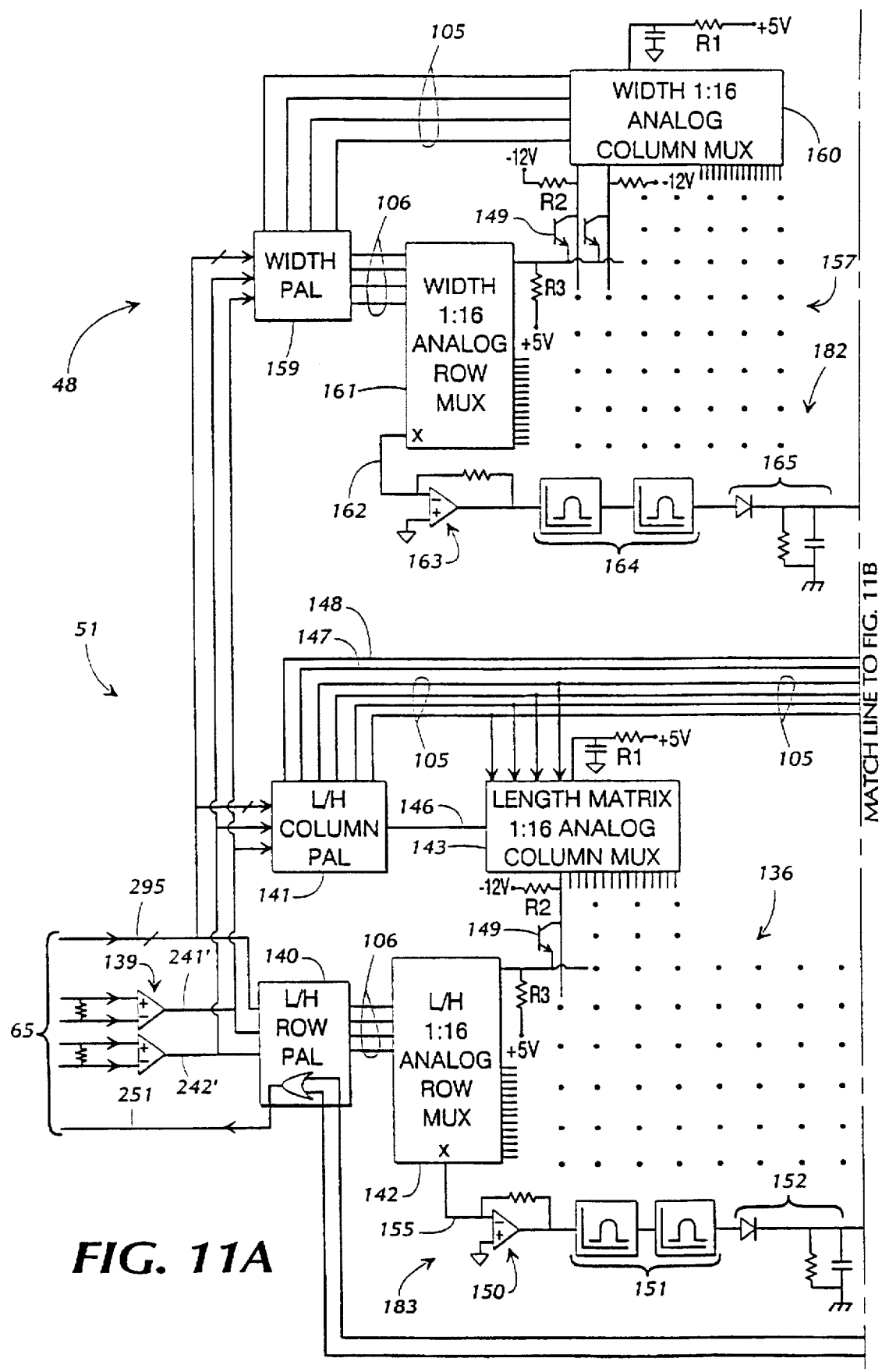
FIG. 11 is a block diagram representation of the right inner IR board and the right front IR board of FIG. 6.
Figure 11B:
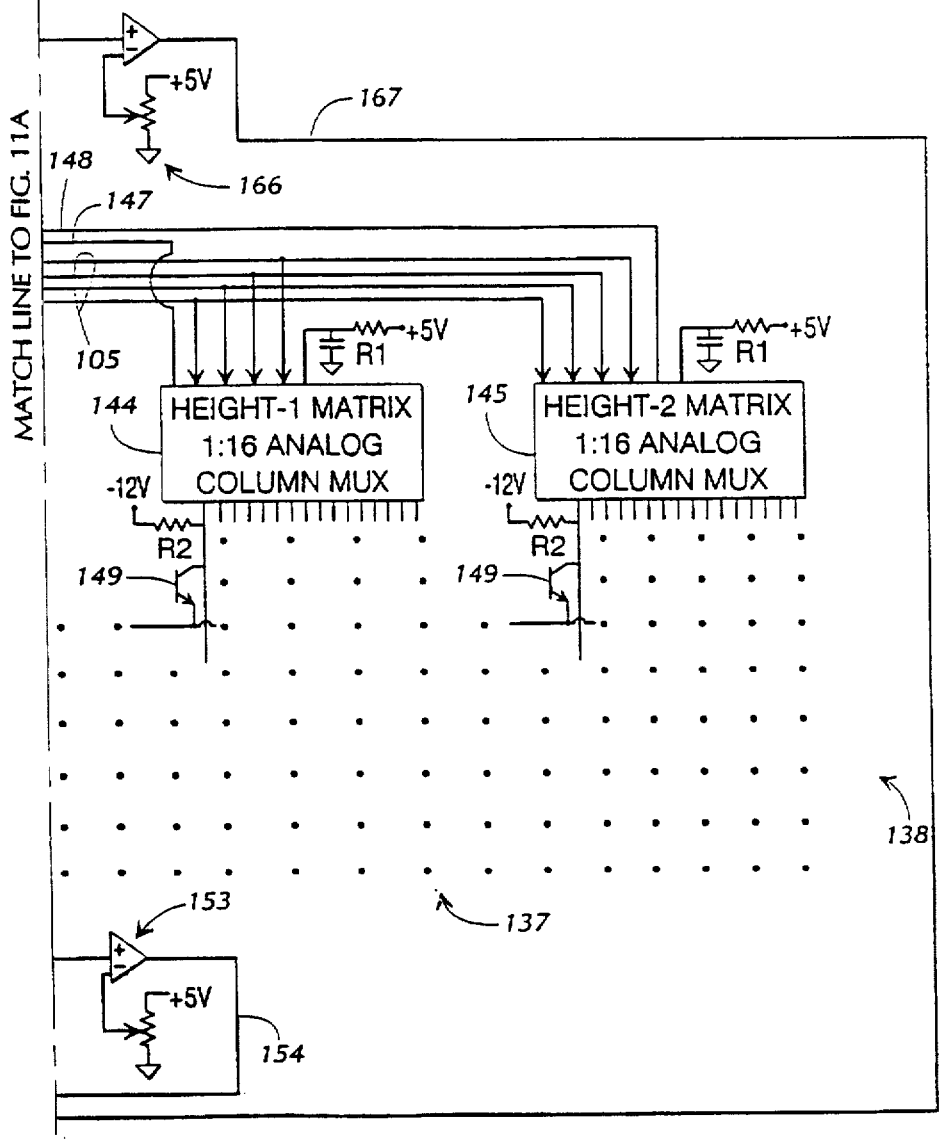

Refer now to FIG. 11, which shows a block diagram representation of the right inner IR board 51 and the right front IR board 48. In a manner very similar to the above discussion, row and column PAL's 140, 141, and 159 are controlled by the right receive matrix select 295 to select a length, width, height-1, or height-2 matrix and activate a row and column based on shifted data from the SPI data line 241'. However, pull up and pull down arrays are not utilized, and the multiplexers are analog multiplexers 142–145, 160–161.

As light is received by a selected phototransistor 149 from one of the receiver arrays 136–138, 157, modulated current flows through a row mux 142, 161 and into a modulation filter 182, 183 to detect the modulated signal. Each modulation filter 182, 183 includes an I-to-V converter 163, 150, two band pass filters 164, 151, a peak detector 165, 152, and a comparator 166, 153. A width IR_seen 167 and a L/H IR_seen 154 are connected to a logical "OR" gate within the L/H row PAL 140 to produce the single right IR_seen line 251 which is connected to the right inner connector 65.

Figure 12:
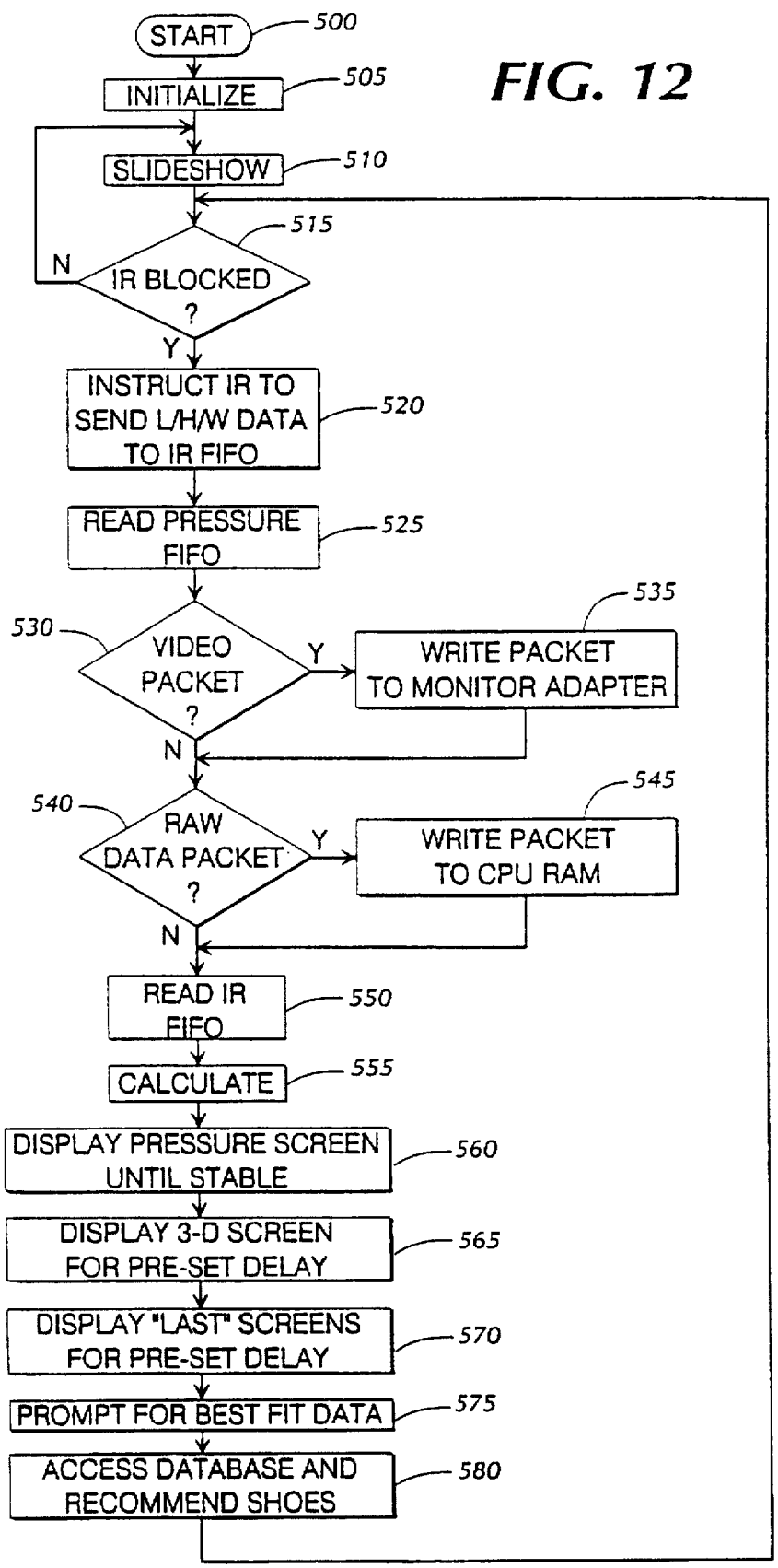
FIG. 12 is a flow chart representation of the steps taken by the controller of FIG. 6.

Refer now to FIG. 12, which shows a flow chart representation of the steps taken by the controller 200 (FIG. 6). For convenience, refer also to FIGS. 6 and 7. After starting at step 500, the controller 200 goes through initialize step 505. Subsequently, an animated slideshow runs in a loop as indicated by decision block 515 until an IR "blocked" packet appears in the IR FIFO 236. The controller programming includes a script means which facilitates modifications to the order and substance of the steps shown in FIG. 12.

After receiving the blocked packet, the controller 200, at step 520, instructs the IR processor 244, through the control register 226, to begin sending length/width/height packets. At step 525, the controller 200 reads the DSP FIFO 227, which continually attempts to write to the DSP FIFO 227, as is discussed in greater detail below. If the pressure packet obtained is a video packet, decision block 530 sends control to step 535 which indicates that the video packet written directly to the monitor adapter 204, having been formatted by the pressure DSP 230, as is discussed in greater detail below. If the pressure packet is a raw data packet, the decision block 540 and step 545 indicate that the data is written into CPU RAM 207 for analysis. Any available IR packets are then read from the IR FIFO 236 into CPU RAM 207 at step 550 for analysis. Calculations are then made at step 555 with all available data from the pressure and IR systems.

Step 560 indicates that a pressure screen is then displayed until the consumer becomes still and the data becomes stable. Subsequent screens, activated by button 28 or timer, include a 3-dimensional screen in step 565, a "last" screen for each foot at step 570, and best fit data prompting screen at step 575. The buttons 28 are used to control screen advancement, printing, and best fit data selections, and the function of each button 28 may be defined to be screen specific and displayed at the base of each screen. After all the data is verified, the controller 200 accesses a database on the hard drive 210, or through the I/O adapter to an external computer, to match available shoes to a particular consumer, defaulting to the larger of the two feet. All of the information obtained may also be recorded and matched to a particular consumer for the shoe provider's future reference.

Figure 13:
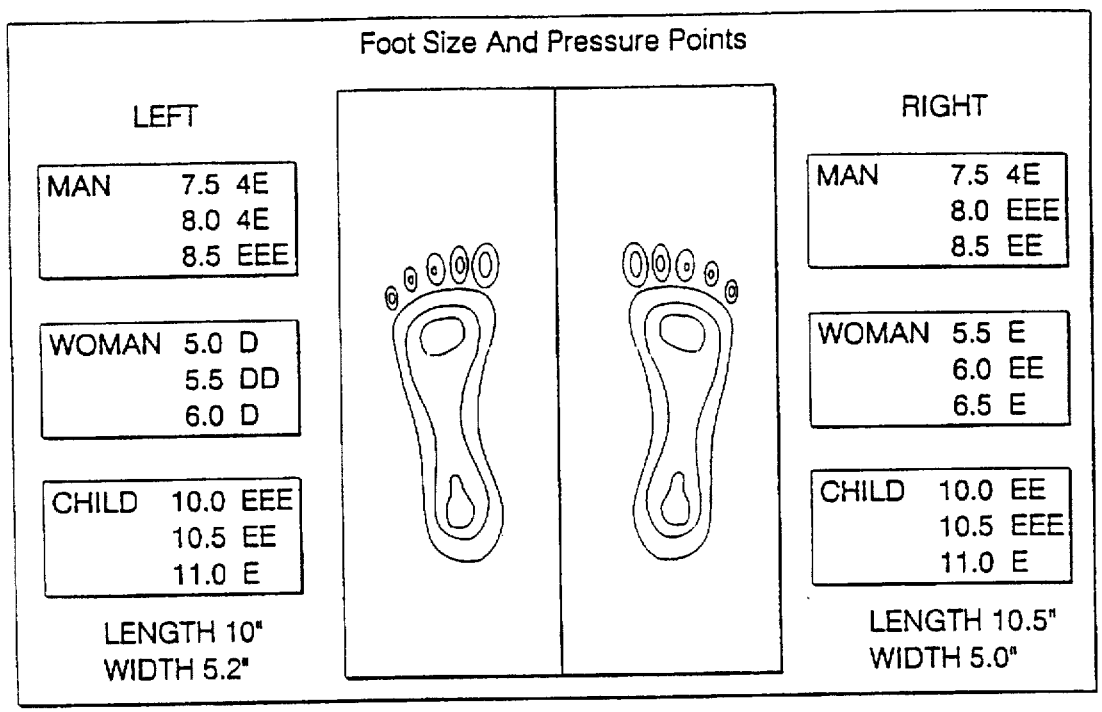
FIG. 13 is a representation of an example of a pressure screen as displayed on the monitor.

One example of an acceptable pressure screen is shown in FIG. 13. All of the data, including the pressure outlines are continually updated while the screen is displayed. Different colors indicated varying amounts of pressure on the pressure outlines. The length and width measurements, derived from the IR packets, for each foot are shown and related to all sizing classes, i.e., man, woman, child, within which ranges the length and width fall. Also, three separate sizes, high medium, and low, for each classification are shown. Adjustments are also made for consumers who stand with feet askew. One method includes comparing the distance from the left-most point to the calculated center of the heel and ball of the foot from the pressure data. If the left-most point is closer to the heel, a ratio is determined based upon the overall width to estimate the actual width. Other methods include calculating angles based on the pressure data to more accurately determine the length and width of an angled foot.

Figure 14:
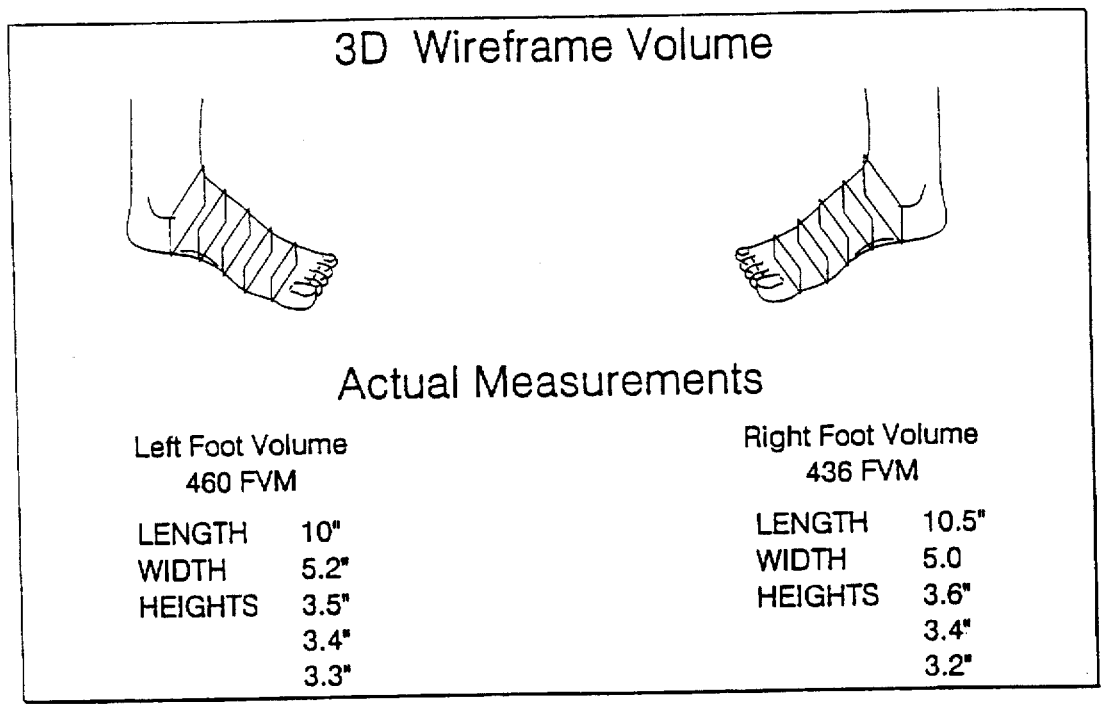
FIG. 14 is a representation of an example of a 3-D wire-frame screen as displayed on the monitor.

FIG. 14 shows an example of an acceptable 3-dimensional screen which sizes a wire-frame model to approximate the size and shape, including arch curvature, of each of the consumer's feet. The volume, length, width, and three characteristic heights of each foot are also displayed. The controller 200 uses both pressure and IR data to compute such measurements. The first height measurement is measured from the base of the leg, the last, at the front end of the height matrix, and the middle, midway between the first and the last height measurements.

Figure 15:
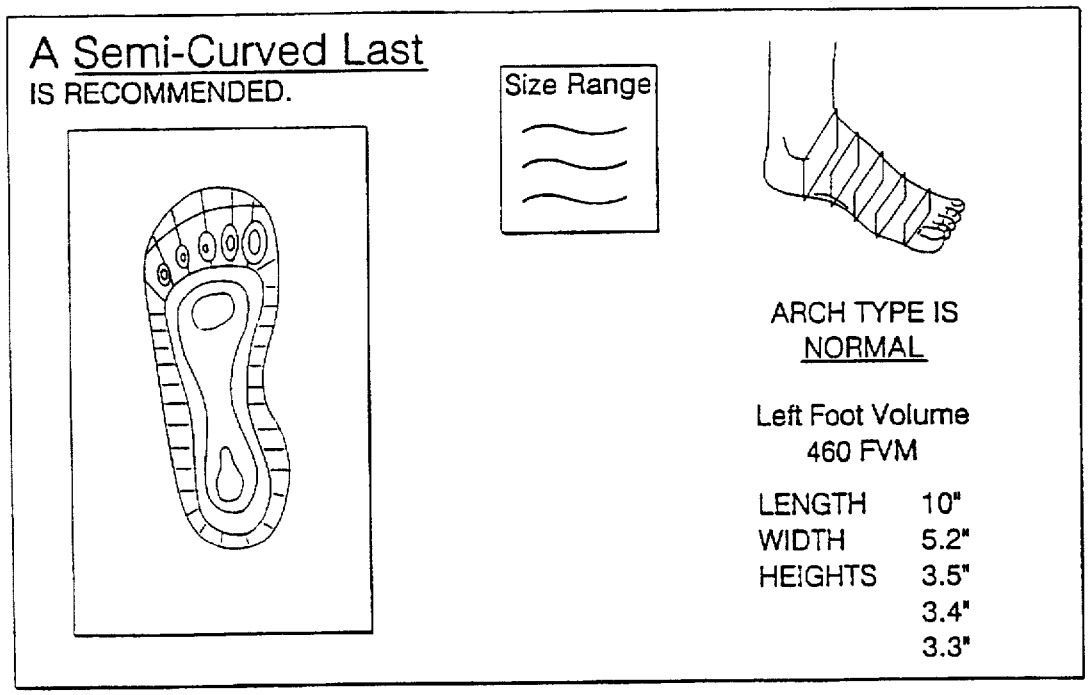
FIG. 15 is a representation of an example of a last screen as displayed on the monitor.
Figure 16:
FIG. 16 is a representation of an example of a best fit screen as displayed on the monitor.

FIG. 15 shows an example of an acceptable "last" screen which includes previously displayed information, along with an arch evaluation and a "last" evaluation based on pronation, and a pressure overlay of an appropriate "last." The relationships between pronation, arches, and "last" recommendations are considered understood by those reasonably skilled in the art. FIG. 16 shows an example of a best fit data prompting screen which prompts the consumer for information relating to the anticipated surface type to be encountered, anticipated activities, correction of computed pronation, and special needs for surface or volume, including whether an arch support is normally used by the consumer.

Figure 17:
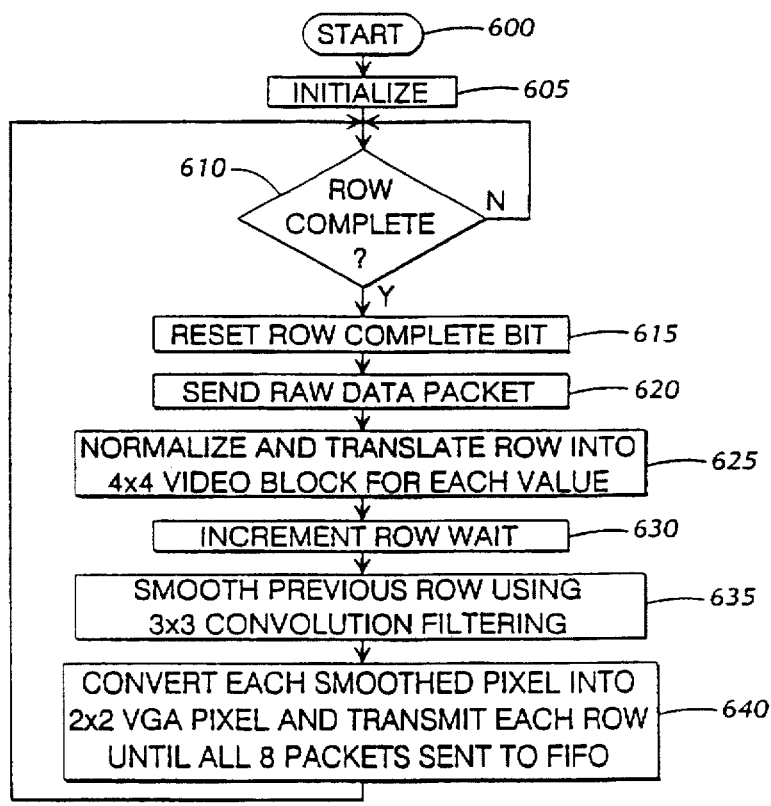
FIG. 17 is a flow chart representation of the steps taken by the foreground processes of the pressure DSP of FIG. 7.

Refer now to FIG. 17, which shows a flow chart representation of the steps taken by the foreground process of the pressure DSP 230 (FIG. 7). For convenience, refer also to FIGS. 6–8. Before the process begins at a start step 600, the controller 200 loads the DSP program memory 224 and resets the pressure DSP 230. During an initialize step 605, the pressure DSP 230 sets variables, timer interrupts, and memory speeds, and copies external variables into internal memory. After initialization, the pressure DSP 230 operates in a tight loop about step 610 which queries whether an entire row has been scanned. After a timer interrupt is set during the initialize step 605, the foreground process is continually interrupted by the timer service routine, shown in FIG. 18.

Figure 18:
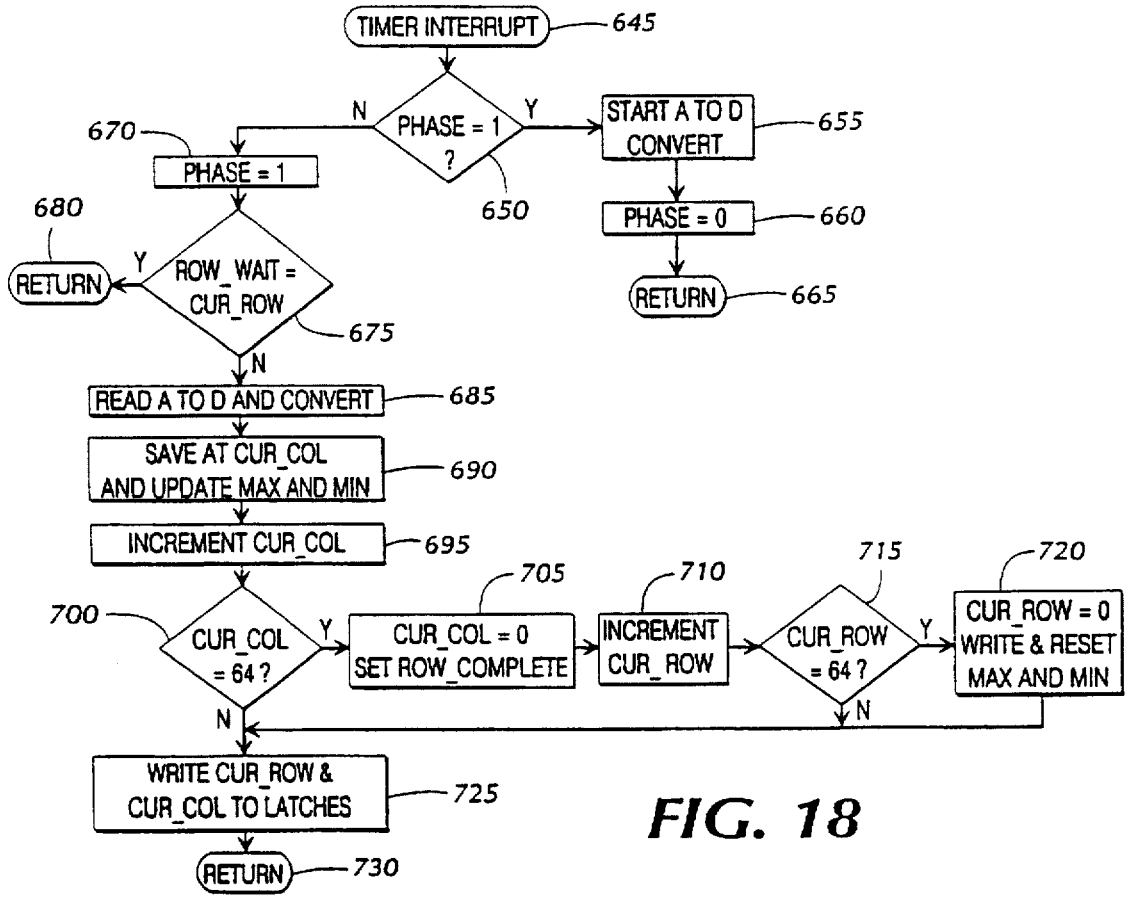
FIG. 18 is a flow chart representation of the steps taken by the timer interrupt service routine of the pressure DSP of FIG. 7.
Figure 19:
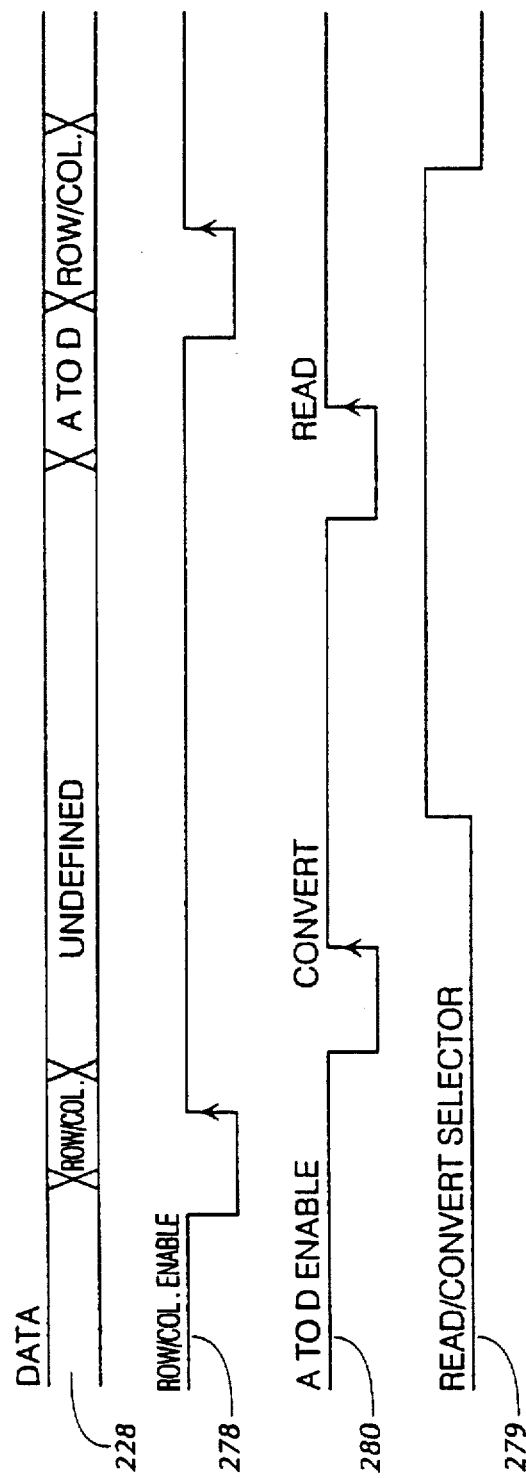
FIG. 19 is a timing diagram of signals present on the pressure sensor control and data lines of FIG. 7.
Figure 20:
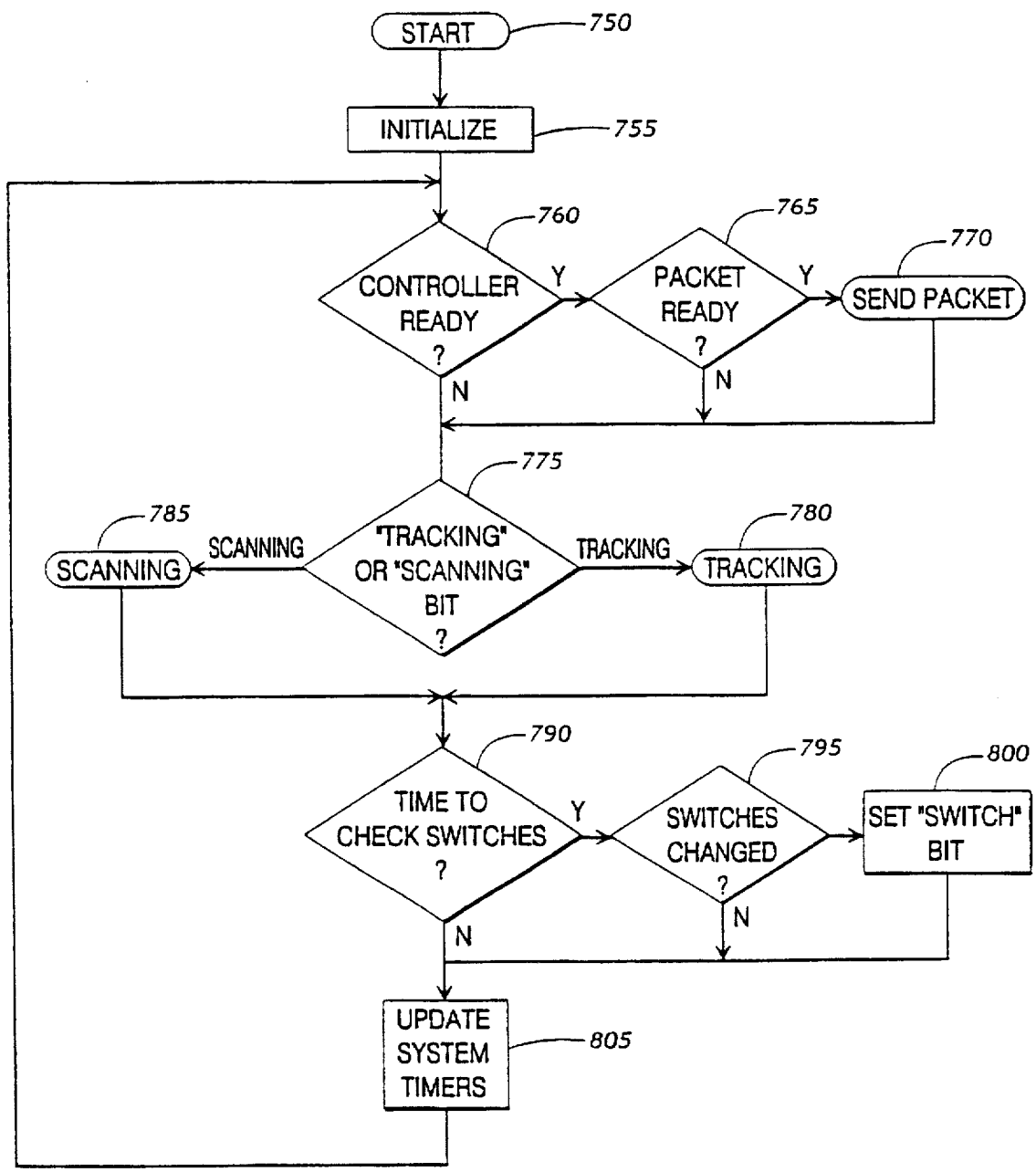
FIG. 20 is a flow chart representation of the steps taken by the control loop of the IR microprocessor of FIG. 7.

Referring also to FIGS. 18 and 19, the timer interrupt service routine 645 begins by determining whether this particular pass through the routine is a "read" pass or a "convert" pass. If a phase variable is set to 1, the Yes branch of decision block 650 is taken to step 655 which indicates that the A-to-D converter 269 is told to begin converting. This is accomplished by pulsing the A-to-D enable line 280 while the read/convert selector 279 is low. As is discussed below with respect to step 725, the current row and column selects were written to the latches 268 and 284 during the previous pass by driving the DSP data bus 228 and pulsing the row/column enable 278. After the A-to-D conversion is started, the phase variable is set to 0 at step 660, and the interrupt routine returns at step 665 to the foreground process in FIG. 17.

During the next timer interrupt, the state of the phase variable will cause control to proceed along the No branch of decision block 650 to step 670 which again sets the phase variable to 1. Subsequently at decision block 675, the variables row_wait and cur_row are checked as a pacing mechanism to prevent the foreground process from overwriting the internal data buffer. If the variables are the same, the routine returns at step 680. If not, step 685 indicates that the timer service routine causes the A-to-D converter 269 to be read and converts the data into appropriate pressure data by referencing one or more tables conversion tables in the program memory 224. The A-to-D read command includes pulsing the A-to-D enable line 280 while the read/convert selector 279 is high.

Step 690 indicates that the pressure value is then saved in the current column location (cur_col) in the data buffer and that max and min variables are updated if the present value is higher or lower, respectively. The current column location is then updated at step 695. If the current column equals 64, the row is complete, and the Yes branch of decision block 700 is taken. Step 705 indicates that the current column location is reset to zero, and the row_complete bit is set. The current row is then incremented at step 710 and evaluated at decision block 715. If the current row equals 64, the current row is reset to zero, and the max and min values are written for foreground process access and reset for interrupt purposes. Ultimately, the current row and column amounts are written to the latches 268 and 284 to scan the next pressure cell.

Referring back to FIGS. 17 and 6–8, when the foreground process sees the row_complete bit, the Yes branch of decision block 610 is taken to step 615 which resets the row_complete bit. At step 620, the pressure DSP 230 prepares and sends a raw data packet to the DSP FIFO 227 and sets a handshaking bit in the control register 226 to signal the controller 200 to read the raw data packet. At step 625, the row of pressure data is normalized and translated into four rows of video data such that each sample of pressure becomes a 4×4 matrix of identical normalized video data.

Normalization produces a more appealing color spectrum on the monitor 24 by scaling for each different consumer. The normalization process includes mapping an actual pressure reading (P) into a video range (min_v to max_v) according to the min and max of the previous scan through each contact board 60, 90 (min_p and max_p). If the pressure reading is below a certain pre-set threshold value, the video value becomes zero. Otherwise, the normalized video value is obtained by the following formula:

$$min\_v+(P-min\_p) * (max\_v-min\_v)/(max\_p-min\_p).$$

After normalization and translation, the row_wait variable is incremented at step 630.

Step 635 indicates that the pressure DSP smoothes then smoothes the previous four video rows (from the previous pressure row) using a 3×3 convolution filtering method, which is considered understood by those skilled in the art of smoothing. At step 640, each row of video data is then converted such that each pixel becomes a 2×2 VGA pixel matrix. Each of the eight rows are then transmitted as vide to packets to the DSP FIFO 227 to be read by the controller 200.

FIGS. 20–25 describe, in flow chart form, the operation of the IR system of the first preferred embodiment of the present invention. For convenience, refer also to FIGS. 6 and 7. As with operation of the pressure DSP 230, the controller 200 first loads the IR RAM 238 before the start step of FIG. 20. After the process begins, the IR processor 244 initializes and queries in decision block 760 whether the controller 200 is ready to receive packets. If so, and a packet is ready to send, decision block 765, (ie., a send_type bit is set) the process jumps to the send packet subroutine 770, discussed in detail below.

Decision block 775 indicates that "tracking" and "scanning" action bits are checked to determine whether the IR system is in tracking or scanning mode. The scanning mode is used when no feet are present in the foot wells, and the tracking mode is used when feet are present, blocking one or more optical signals. Control is then transferred to the appropriate tracking or scanning subroutines 780, 785, discussed in detail below. Decision blocks 790 and 795 indicates that the status of the switches 28 are checked periodically. If the status has changed, the "switch" bit is set in a send_type byte which identifies ready packet types. Subsequently, the system timers are updated in step 805.

Figure 21:
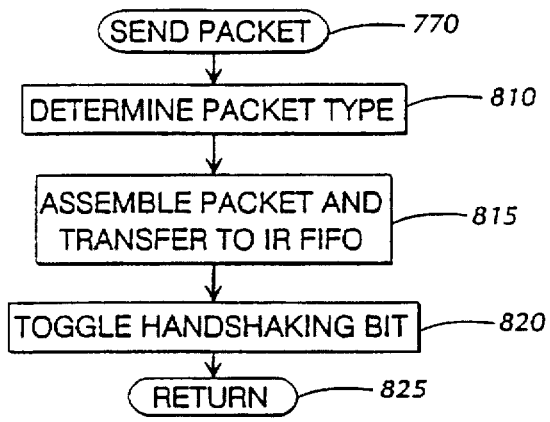
FIG. 21 is a flow chart representation of the steps taken by the send packet subroutine of the IR microprocessor of FIG. 7.

FIG. 21 shows a flow chart representation of the send packet subroutine 770. The packet type to be assembled and sent is first determined in step 810 based on the send_type byte. At step 815 the packet is assembled and transferred to the IR FIFO 236. Step 820 indicates that the handshaking bit in the control register 226 is toggled to notify the controller 200 that a packet is available. Subsequently, control is returned in step 825.

Figure 22:
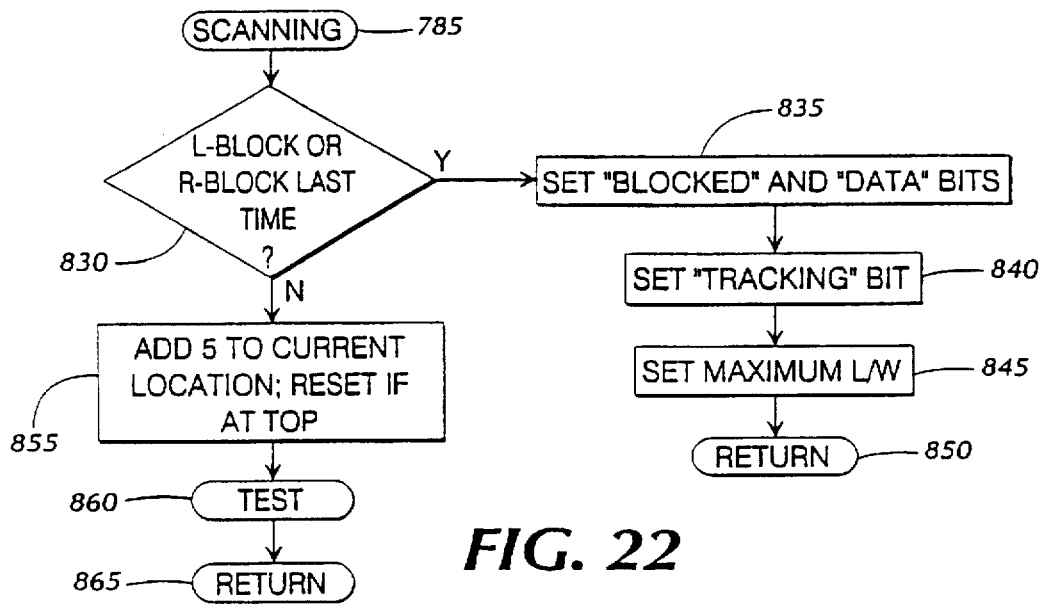
FIG. 22 is a flow chart representation of the steps taken by the scanning subroutine of the IR microprocessor of FIG. 7.

FIG. 22 is a flow chart representation of the scanning subroutine 785. According to step 830, if an l-block or r-block bit was set during the previous scan, the "blocked" and "data" send_type bits are set, as indicated by step 835. The "tracking" bit is set at step 840, and length and width variables are reset to maximum values at step 845. Control is then returned at step 850. If an l-block or r-block bit was not set during the previous scan, step 855 indicates that the current location is incremented by 5 or reset if at the end. The test subroutine 860 is then called, followed by a return at step 865.

Figure 23:
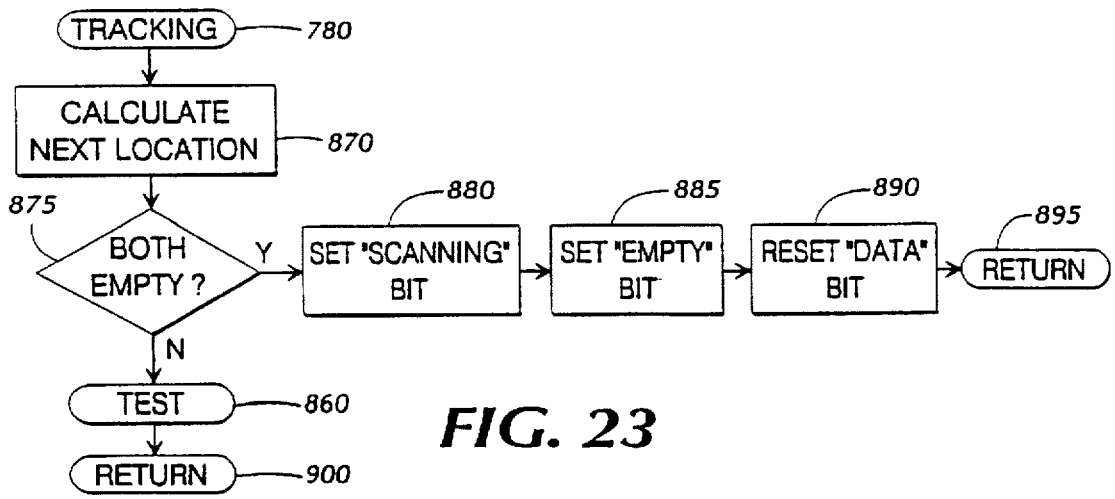
FIG. 23 is a flow chart representation of the steps taken by the tracking subroutine of the IR microprocessor of FIG. 7.

FIG. 23 shows the tracking subroutine 780 which indicates that the next location is first calculated at step 870. This step represents a "dithering" method which, with respect to one end of one line of an array, such as the length, width, or a physical height column, moves inward from the outer most boundary until encountering a blocked signal, moving backward until the signal is cleared, and again moving inward until encountering another blocked signal, thus tracking the boundary. The method rotates through the arrays and keeps track of each boundary for each array line for each foot. Upon encountering boundaries, the values are saved for placement in the data packets.

After the next locations are calculated, the tracking subroutine checks to see if both foot wells 40, 70 (FIG. 1) are empty by comparing the last calculated boundaries. If empty, the "scanning" action bit and "empty" send_type bits are set, and the "data" send_type bit is reset. Control is then returned at step 895. If not empty, the test subroutine 860 is initiated, followed by a return 900.

Figure 24:
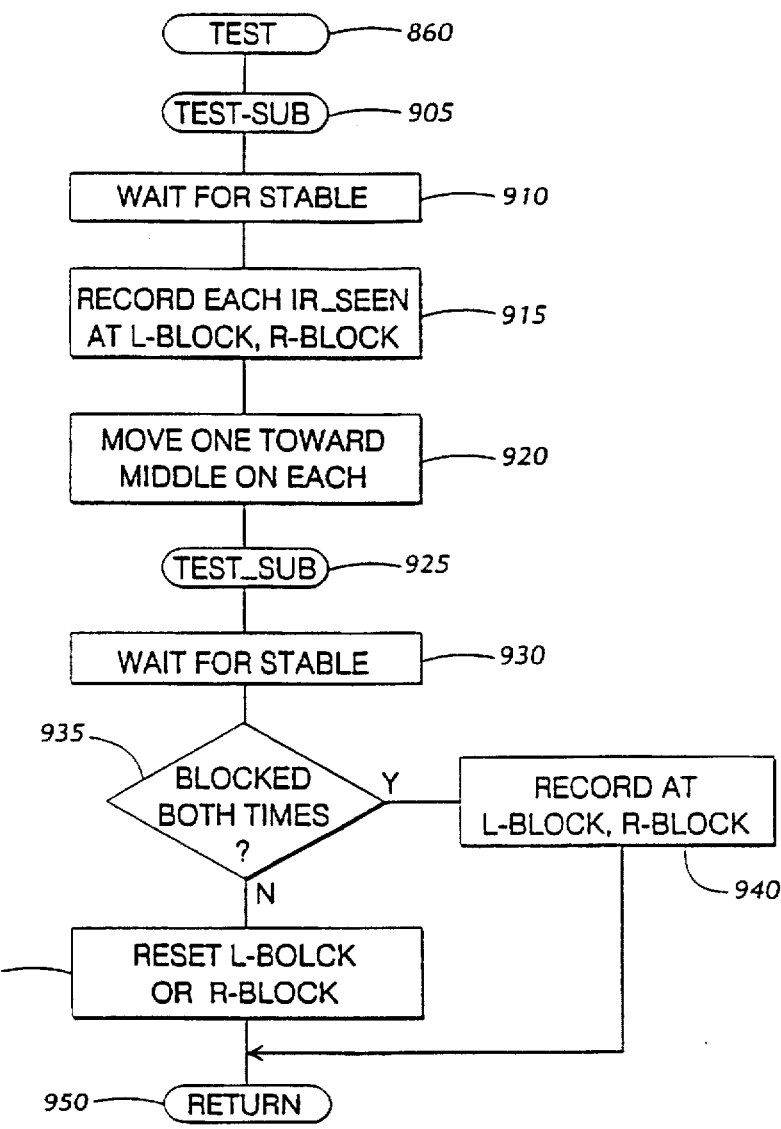
FIG. 24 is a flow chart representation of the steps taken by the test subroutine of the IR microprocessor of FIG. 7.
Figure 25:
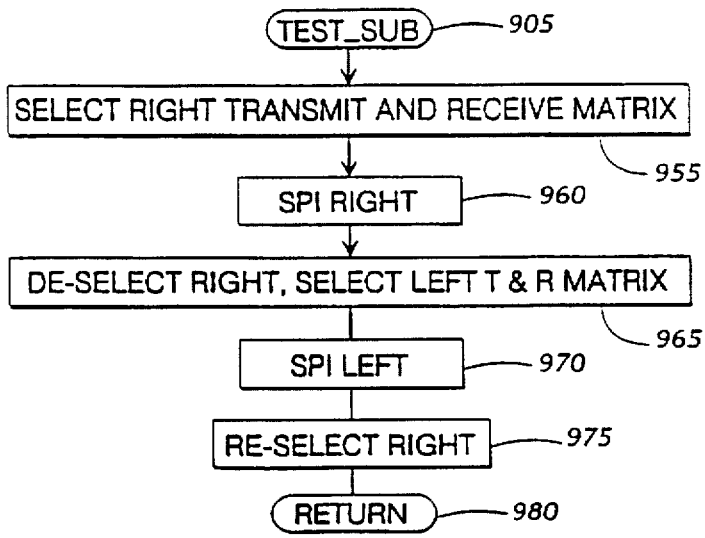
FIG. 25 is a flow chart representation of the steps taken by the test subroutine of the IR microprocessor of FIG. 7.

FIG. 24 represents the test subroutine 860 and immediately calls the test_sub subroutine at step 905 which is shown in FIG. 25. According to FIG. 25, the test_sub subroutine 905 selects a right transmit and right receive matrix at step 955 and sends transmitter and receiver selection data out on the SPI data line 241 to the selected right matrix. In the preferred embodiments, corresponding transmitter and receiver are selected. However, alternate embodiments include selecting non-corresponding pairs to derive additional types of data. The right matrixes are then disabled, and the left transmit and receive matrixes are selected and sent SPI data according to steps 965 and 970. Subsequently, the right matrixes are re-selected at step 975, and control is returned to the test subroutine at step 980.

Step 910 in FIG. 10 indicates that the IR processor 244 waits for a stable signal and then records the results of each IR_seen 251, 252 at the l-block and r-block bits at step 915. The test subroutine 860 then begins a process of determining whether an actual boundary, rather than trash or an error, has been encountered. At step 920, one location closer inward is calculated for both the left and right system and tested in test_sub at step 925, followed by another wait at step 930. If blocked both times, l-block or r-block are set at step 940, or reset at step 945 if not blocked both times. Control is then returned at step 950.

Figure 26:
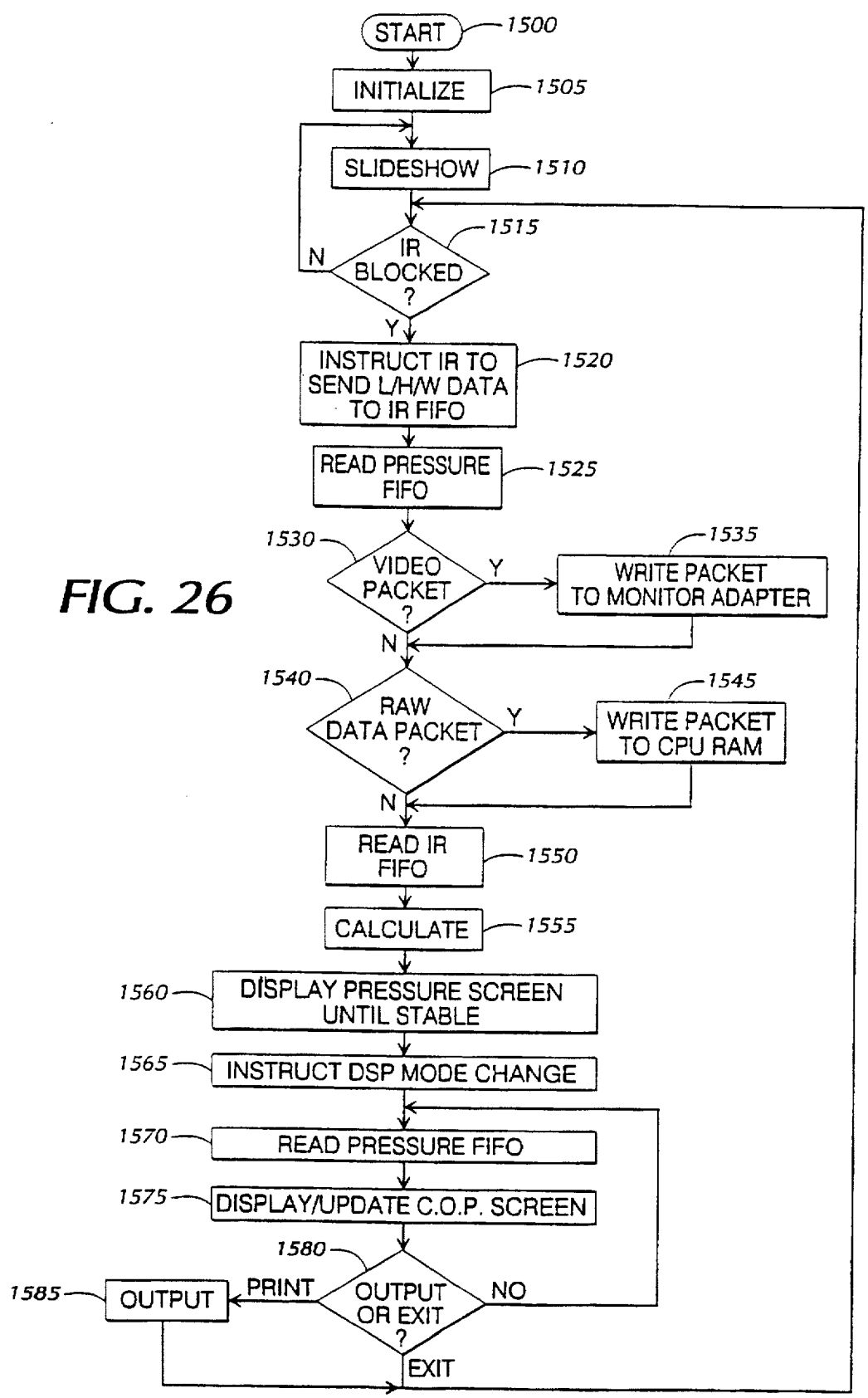
FIG. 26 is a flow chart representation of the steps taken by the controller of FIG. 6 according to a second preferred embodiment of the present invention which shows a pressure distribution screen and a center of pressure screen.
Figure 27:
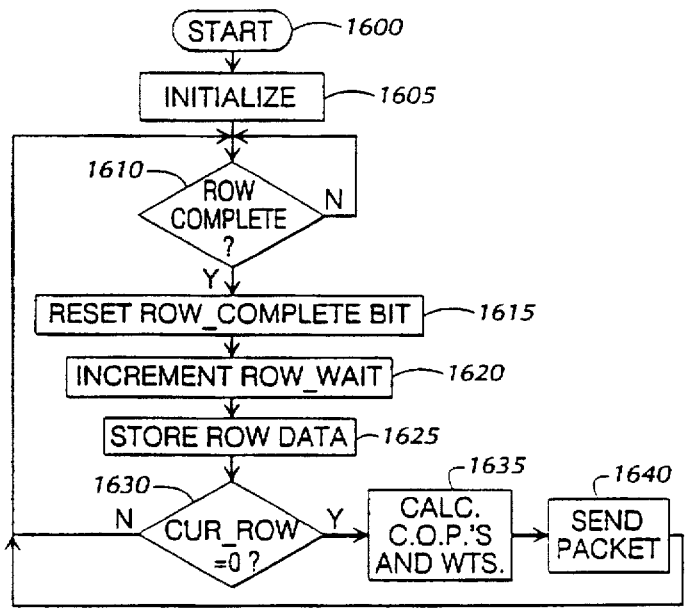
FIG. 27 is a flow chart representation of the steps taken by the foreground processes of the pressure DSP of FIG. 7 according to the second preferred embodiment of FIG. 26.
Figure 28:
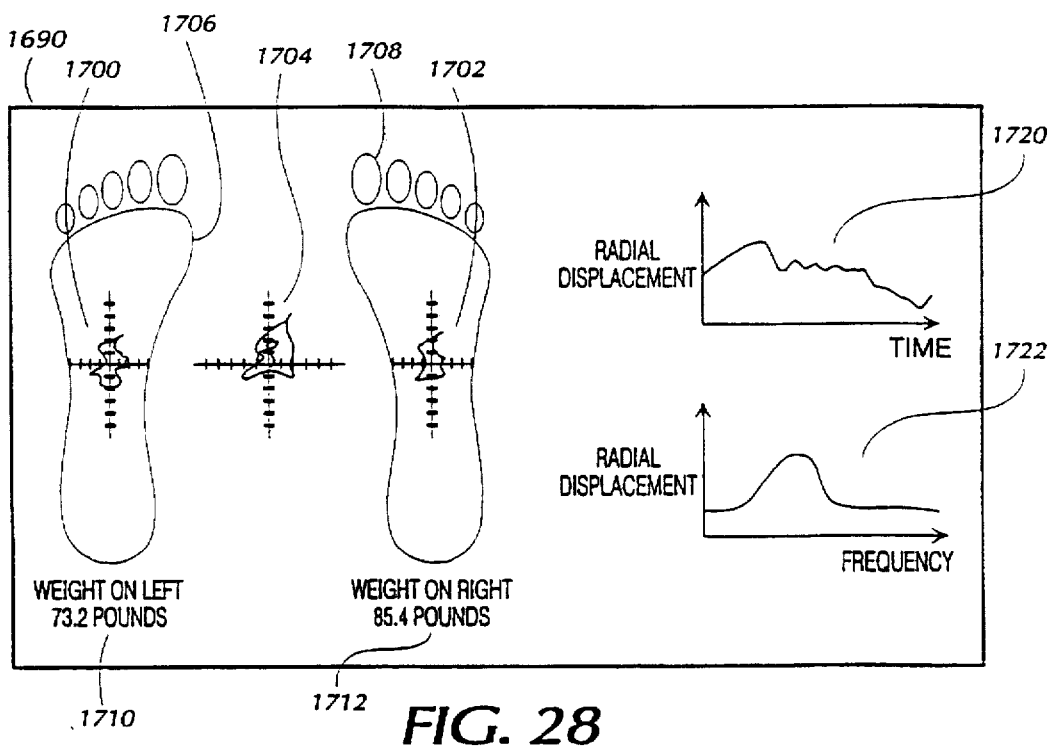
FIG. 28 is a representation of an example of a center of pressure screen as displayed on the monitor.

Refer now to FIGS. 26–28 which refer to a second preferred embodiment of the present invention. The foot analysis system (not shown) of this second preferred embodiment is different from the foot analysis system 20 (FIG. 1) of the first preferred embodiment only in terms of programming in the various programmable devices contained therein, thus references will be made to apparatus elements of the foot analysis system 20 for ease of explanation. FIG. 26 shows a flow chart representation of the steps taken by the controller 200 (FIG. 6) according to the second preferred embodiment of the present invention. Steps 1500–1560 are identical to similarly placed steps in FIG. 12 of the first preferred embodiment of the present invention. Thus, one or more default screens are displayed until the foot analysis system 20 detects a foot, after which a pressure distribution screen is displayed at step 1560. The pressure distribution screen, such as that shown in FIG. 13, is continually updated and displayed until a relative degree of stability is reached by the user, thus, step 1560 is understood to include a loop of steps similar to steps 1520–1555.

During and before step 1560, the pressure DSP 230 (FIG. 7) operates in a pressure distribution mode as initialized. At step 1565, the controller 200 instructs the pressure DSP 230 (FIG. 7) to change into a center of pressure (COP) mode to begin calculating centers of pressure and weight information as shown in FIG. 27. Referring now to FIG. 27, the foreground processes of the pressure DSP 230 beginning at step 1600 are much faster in the COP mode since video data is not being calculated. The overall scanning speed is designed to be fast enough to ensure accurate measurements of postural sway. The interrupt service routine for the foreground processes of FIG. 27 are identical to those of the pressure distribution mode of FIG. 18. According to FIG. 27, after steps which are similar to steps previously discussed in reference to FIG. 17, each row of data is stored (step 1625) and used in calculating centers of pressure and total weight supported by each foot after all of the rows are scanned (step 1635). Subsequently, a packet is assembled and sent to the pressure (DSP) FIFO 227 (FIG. 7). Weight data can be calculated through a standard multiplication factor, or individual calibration of separate sensors can be employed to determine the correlation between sensor value and actual weight for each pressure sensor. A standard two-dimensional centroid summation formula including weighted averages which would be understood by those reasonably skilled in the art is used to determine each of the displayed mathematical centers of pressure.

Referring back to FIG. 26, the controller 200 reads the pressure FIFO 227 (step 1570) and performs necessary calculations to display on the monitor 24 (FIG. 1) a center of pressure (COP) screen (step 1575), an example of which is shown as screen 1690 in FIG. 28. Referring now to FIG. 28, the COP screen 1690 shows three center of pressure (COP) grids, including a left foot COP grid 1700 positioned relative to a left foot outline 1706, a right foot COP grid 1702 positioned relative to a right foot outline 1708, and a combined COP grid 1704 located between the foot outlines 1706 and 1708. The axis lines for the left foot COP grid 1700 and the right foot COP grid 1702 are placed at the first center of pressure coordinates received from the pressure DSP 230 relative to each respective foot outline 1706, 1708. In one embodiment, the foot outlines 1706, 1708 correspond to the perimeter of the foot outlines in the stable pressure distribution screen of FIG. 12. In another embodiment, the outlines 1706, 1708 are standard shapes, and in yet another embodiment, the outlines 1706, 1708 are modified standard shapes incorporating actual IR and pressure measurements.

The COP screen 1690 also includes weight measurements corresponding to each foot. By displaying the information adjacent the foot outlines 1700, 1702, a user is readily able to correlate COP information with weight distribution between feet. In addition, the COP screen 1690 includes a radial displacement time graph 1720 and a radial displacement frequency graph 1722. In effect, the radial displacement is the calculated distance from the origin of the combined COP grid 1704. In alternate embodiments, the graphs 1720 and 1722 also include "X" and "Y" components of the radial displacement, and additional graphs include various common derivatives and transforms of the displacement. As shown in FIG. 28, each COP grid 1700, 1702, 1704 includes a trace pattern as the centers of pressure move through time and the screen 1690 is continually updated (the "No" branch of decision block 1580 of FIG. 26). Through the control buttons 28a–e, as with various other user input, a user is provided the ability to disable the tracing function, as well as the ability to refresh the screen at any point. In addition, a user is able to identify a patient (through manual input or electronic communication from a local or remote connected computer of a patient number or time of last test) and overlay past results on the screen 1690 so that comparisons can be made by the user to measure progress, etc. Step 1585 indicates that the foot analysis system is able to, at the user's request, output screen and/or testing result information to a printer, magnetic media, or another connected computer for further analysis or storage.

Depending on particular testing needs, instructional information (e.g. "Close your eyes now", "Place your left foot forward and your right foot backward", "Wiggle your toes", or "Shift your weight forward onto your toes") and test result information may also be displayed (e.g. "You possess a normal ability to walk and keep your balance", "You still need your walker", "Your medicine should be changed to...", or "You are swaying less than your previous test"). According to an alternate embodiment of the present invention, the detection of excessive movement by a patient during the COP mode causes the foot analysis system to re-enter the pressure distribution mode (step 1560) before returning back to the COP mode to proceed. Additionally, the user is able to manually alternate between the two modes.

It should be clear that the foot analysis system of the present invention is able to compute a variety of medically useful results related to center of pressure, postural sway, and weight distribution. Accordingly, a variety of medical conclusions can be drawn more objectively and accurately based upon information displayed by the present invention. In addition, since the foot analysis system of the present invention locates all sides of the foot, regardless of whether one or more sides is placed against a wall or edge, the present invention is particularly useful in medical tests including various, relatively random foot positions, such as with handicapped patients. Also, while the frame structure 22 (FIG. 1), because of its shape, can be useful to anyone needing extra support to maintain balance, the frame structure 22 can be particularly useful with patients needing extra support. In addition, the present invention also includes alternate embodiments which include additional IR sensors to provide layers of horizontal measurements, as well as more vertical data points along the length and width of the feet. Furthermore, sway can also be measured with IR sensor by monitoring leg movement. Also, while FIG. 13 shows one acceptable method of displaying a pressure grid, others methods are also included, such as two- and three-dimensional bar graphs of one to many different colors varying with pressure levels.

Figure 29:
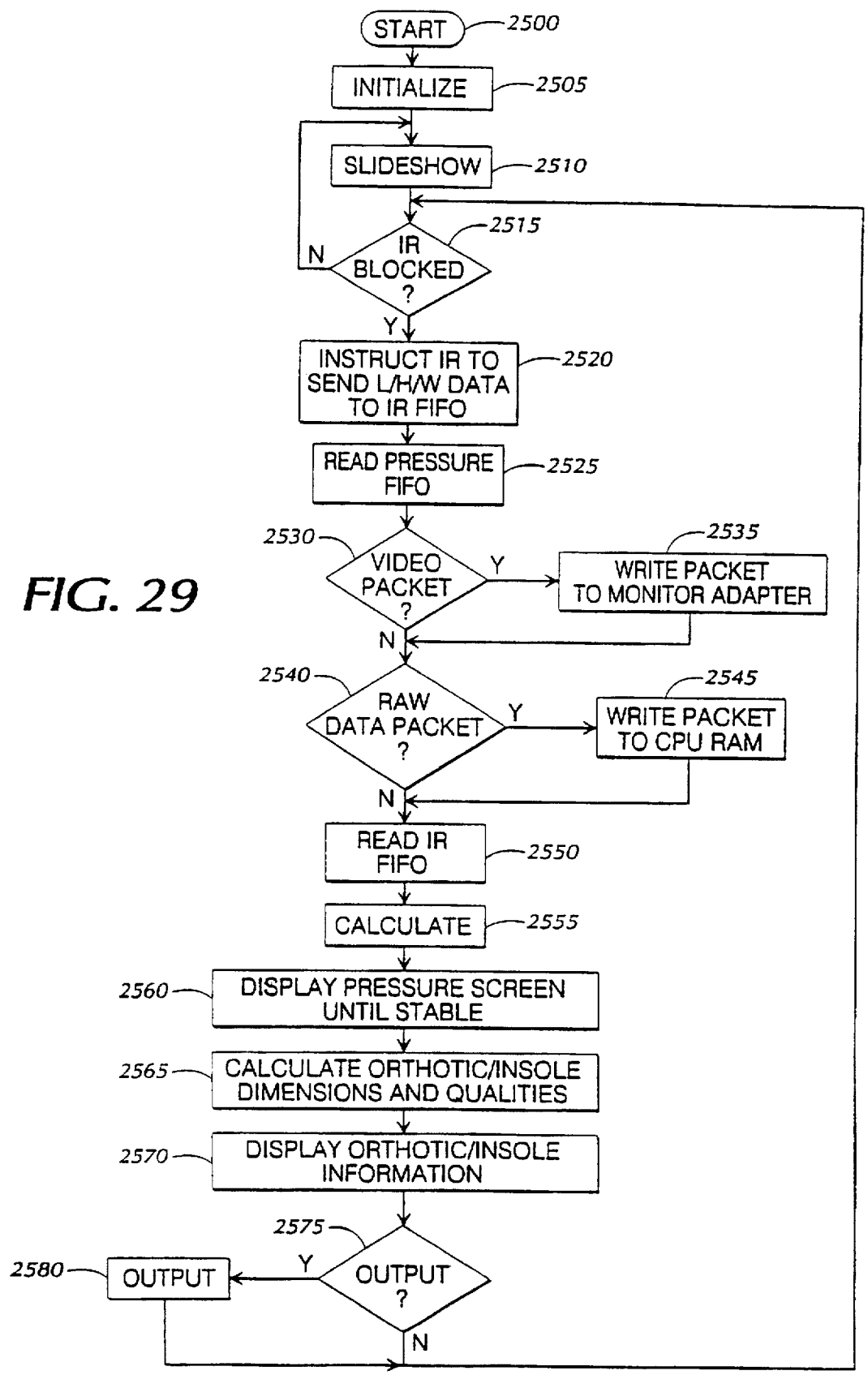
FIG. 29 is a flow chart representation of the steps taken by the controller of FIG. 6 according to a third preferred embodiment of the present invention which shows a pressure distribution screen and an orthotic screen.
Figure 30:
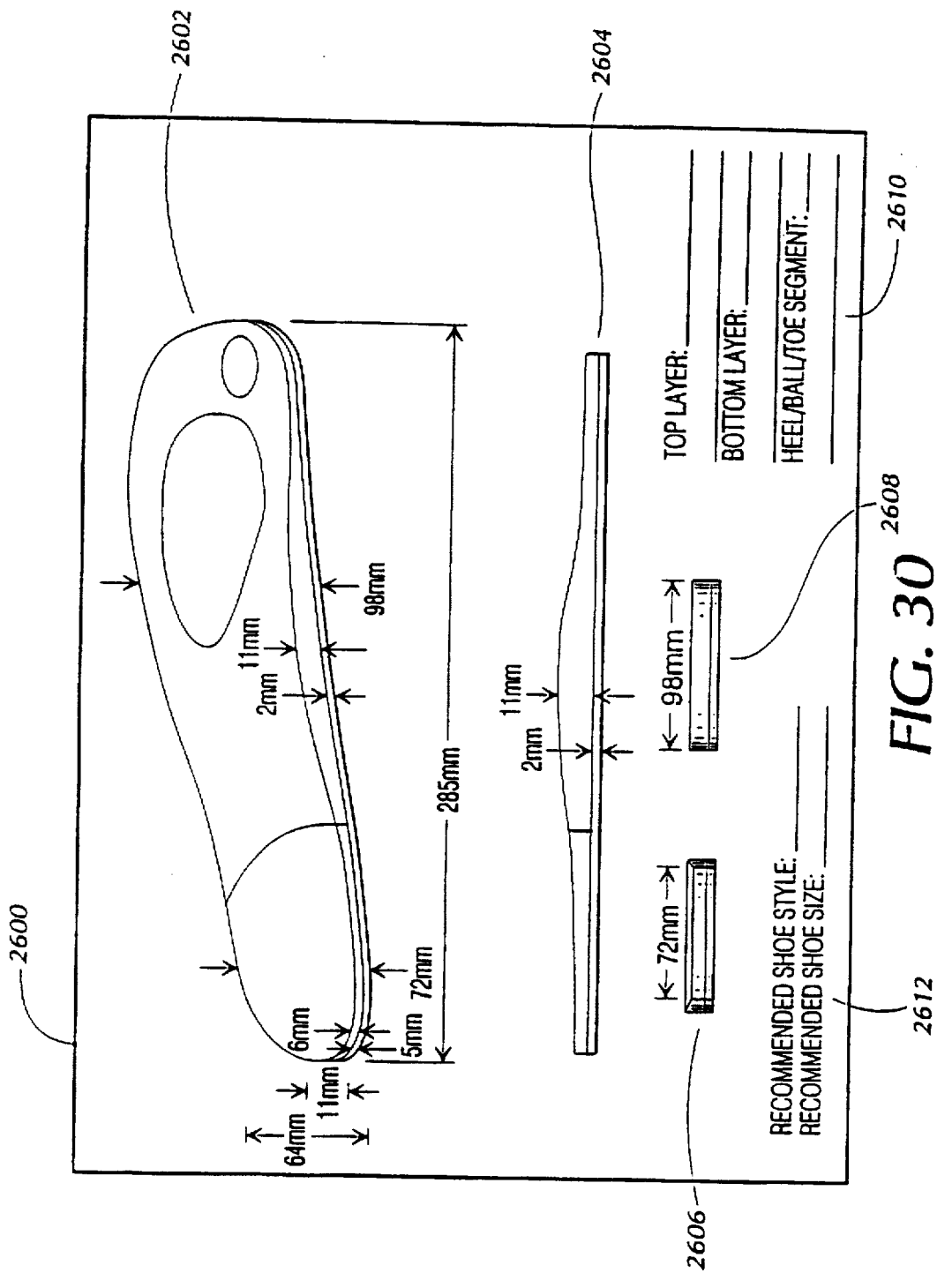
FIG. 30 is a representation of an example of an orthotic screen as displayed on the monitor.

Refer now to FIGS. 29 & 30 which relate to a third preferred method of the present invention for prescribing a custom orthotic or selecting an insole from a stock of standard insoles. The foot analysis system (not shown) of this third preferred embodiment is also different from the foot analysis system 20 (FIG. 1) of the first preferred embodiment only in terms of programming in the various programmable devices contained therein, thus references will again be made to apparatus elements of the foot analysis system 20 for ease of explanation. FIG. 29 shows a flow chart representation of the steps taken by the controller 200 (FIG. 6) according to the third preferred embodiment of the present invention. Steps 2500–2560 are identical to similarly placed steps in FIG. 12 of the first preferred embodiment of the present invention. Thus, one or more default screens are displayed until the foot analysis system 20 detects a foot, after which a pressure distribution screen is displayed at step 2560. The pressure distribution screen, such as that shown in FIG. 13, is continually updated and displayed until a relative degree of stability is reached by the user, thus, step 2560 is understood to include a loop of steps similar to steps 2520–2555.

Next, the foot analysis system calculates (step 2565) dimensions and qualities of recommended custom orthotics or stock insoles and displays visual representations of the orthotics or insoles (step 2570) before outputting more detailed prescription or selection information (step 2580). During step 2565, a user is prompted for certain information, such as whether the foot analysis system is to recommend custom orthotics or stock insoles, which type of activies are planned by the user, what type of shoes and styles are currently being worn. First, pressure and IR data are analyzed to compute a variety of measurements and values, such as distributed weight values throughout each foot, overall weight, foot length, foot width, foot heights at various locations along the foot, and foot volume. The above-discussed alternate embodiment which employs additional height-measuring IR sensors along the length of the foot would be particularly useful for detecting bunions, toe deformities etc. toward the front of a foot which could interfere with shoe comfort. After the variety of measurements and values are computed, they are compared with stored information related to shoe size and available shoe volume, as well a variety of properties of various orthotic/insole materials, such as properties related to cushioning, force absorption, deflection, compression, rigidity, etc. The comparison attempts to design an orthotic or an insole for each foot which best distributes forces encountered by the foot. The sizes of the orthotics or insoles are, of course, affected by shoe dimensions and available volume. Thus, it is desirable to have actual shoe dimensions and available shoe volume. If such values are not available, estimates can be made based upon average volumes since the appropriate shoe size will have been previously calculated. If current shoe sizes or styles are inappropriate or harmful for the recommended orthotic or insole, a new shoe size or style is recommended and used in the orthotic/insole calculations. It is also understood that composite orthotics can be designed which include multiple layers or sections of different types of material which extend partially or completely from top to bottom or heel to toe of the orthotic. Composite orthotics are often desirable since different construction materials are more effective at meeting various foot needs such as absorbing shock, cushioning, etc. In designing composite orthotics, the shape and various thicknesses of each layer and section are also calculated.

Refer now to FIG. 30 which shows a representation of an example of an orthotic/insole screen 2600. Various views, including a perspective view 2602, a side view 2604, a rear view 2606, and a front view 2608 are shown including various example dimensions. An identification and description of the layer/section materials 2610 is also provided. Since only one orthotic for one foot is represented in screen 2600, a subsequent similar screen would show the orthotic for the other foot. Alternately, both orthotics could be shown on one screen. A shoe recommendation section 2612 indicates the shoe size and shoe style appropriate for accommodating and protecting the user's feet based upon all of the measured and input factors, including foot size and volume, weight, activity, etc.

Referring back to FIG. 29, prescriptive output information (step 2580) will be much more detailed to describe the exact dimensions of the prescribed orthotics. It should be clear that the present invention is able to prescribe very customized orthotics in an objective and accurate method, yet easy to use, method. Regarding the selection of stock insoles, alternate embodiments include simply supplying a brand name and a size for the selected insole without displaying any graphical representations of the insoles.

While the embodiments of the present invention which have been disclosed herein are the preferred forms, other embodiments of the method and apparatus of the present invention will suggest themselves to persons skilled in the art in view of this disclosure. Therefore, it will be understood that variations and modifications can be effected within the spirit and scope of the invention and that the scope of the present invention should only be limited by the claims below.

We claim:

1. A method of diagnosing or monitoring those medical problems in humans which are detectable or monitorable by analyzing data tending to indicate how a patient's body supports itself, the method comprising the steps of:

arranging a plurality of optical sensors to partially define a measurement zone employable to quantify movement of a patient's lower leg relative to a respective foot;

arranging a plurality of pressure sensors in a pressure sensor matrix beneath said measurement zone to quantify the amount of force applied to individual pressure sensors by different portions of a patient's foot;

receiving a patient's lower leg within the measurement zone and the foot associated with the lower leg in at least indirect contact with the plurality of pressure sensors;

operating the plurality of optical sensors at a first time to generate a first set of optical data corresponding to a position of the lower leg received within the measurement zone;

operating the plurality of pressure sensors at the same first time to generate a first set of force measurements corresponding to the portion of the patient's weight supported by different portions of the patient's foot and different pressure sensors beneath the different portions of the patient's foot;

computing from the first set of optical data a first position of the patient's lower leg relative to the foot associated with the patient's lower leg;

computing from the first set of force measurements a first plurality of centers of pressure, each center of pressure being associated with a different portion of the patient's foot;

instructing the patient on a video display to perform a physical action;

operating the plurality of optical sensors at a second time after performance of the physical action to generate a second set of optical data corresponding to a second position of the lower leg received within the measurement zone;

operating the plurality of pressure sensors at the same second time to generate a second set of force measurements corresponding to the portion of the patient's weight supported by different portions of the patient's foot and different pressure sensors beneath the different portions of the patient's foot;

computing from the second set of optical data a second position of the patient's lower leg relative to the foot associated with the patient's lower leg;

computing from the second set of force measurements a second plurality of centers of pressure, each center of pressure being associated with a different portion of the patient's foot;

analyzing similarities and differences in the first and second positions of the patient's lower leg and in the first and second pluralities of centers of pressure to determine a test result; and, presenting the test result via the video display to the patient.

2. The method of claim 1 wherein the method further comprises a step of displaying on a video display a first image representative of the first plurality of centers of pressure overlaid on a second image representative of the second plurality of centers of pressure.

3. The method of claim 1 wherein the method further comprises the steps of: producing a first set of test result data by performing the steps of operating, computing, and instructing on a first day; producing a second set of test result data by performing the steps of operating, computing, and instructing on a second day; and, determining the patient's progress on a particular treatment regimen by comparing the data of the first and second sets of test result data.

4. The method of claim 1 wherein the test result comprises a determination of the patient's postural sway.

5. The method of claim 1 wherein the test result comprises a determination of the patient's balance.

6. The method of claim 1 wherein the method further comprises a step of displaying on a video display an image representative of the portions of the patient's weight which are distributed to respective portions of the patient's foot.

7. The method of claim 1 wherein the method further comprises a step of displaying on a video display an image representative of a plurality of centers of pressure relative to an plan view outline of the patient's foot.

8. The method of claim 7 wherein the method further comprises the steps of: arranging, receiving, operating, computing, and analyzing with respect to both of the patient's lower legs and respective feet; and, displaying on a video display an image representative of the plurality of centers of pressure for both feet.

9. The method of claim 1 wherein the method further comprises the steps of: continuously performing the steps of operating, computing, and analyzing over a period of time; and, displaying on a video display an image representative of a plurality of centers of pressure relative to a time axis.

* * * * *